(12) United States Patent
Smith

(10) Patent No.: US 12,055,534 B2
(45) Date of Patent: Aug. 6, 2024

(54) ANALYSIS OF RELEASE-RESISTANT WATER IN MATERIALS AND RELATED DEVICES AND METHODS

(71) Applicant: Michael P. Smith, Tulsa, OK (US)

(72) Inventor: Michael P. Smith, Tulsa, OK (US)

( * ) Notice: Subject to any disclaimer, the term of this patent is extended or adjusted under 35 U.S.C. 154(b) by 329 days.

(21) Appl. No.: 17/374,912

(22) Filed: Jul. 13, 2021

(65) Prior Publication Data
US 2021/0341455 A1 Nov. 4, 2021

Related U.S. Application Data

(63) Continuation-in-part of application No. PCT/US2020/013261, filed on Jan. 12, 2020.

(60) Provisional application No. 62/791,879, filed on Jan. 13, 2019.

(51) Int. Cl.
| | |
|---|---|
| G01N 33/24 | (2006.01) |
| E21B 49/08 | (2006.01) |
| G01L 9/00 | (2006.01) |
| G01N 1/28 | (2006.01) |

(52) U.S. Cl.
CPC ......... *G01N 33/246* (2013.01); *E21B 49/081* (2013.01); *G01L 9/0095* (2013.01); *G01N 1/286* (2013.01)

(58) Field of Classification Search
CPC .. G01N 33/246; G01N 1/286; G01N 33/2823; E21B 49/081; G01L 9/0095
USPC ............... 73/73, 76, 152.03, 152.04, 152.08; 175/40, 48, 50, 58–60; 166/250.01, 166/250.16, 264
See application file for complete search history.

(56) References Cited

U.S. PATENT DOCUMENTS

| | | |
|---|---|---|
| 4,495,414 A | 1/1985 | Barrie |
| 4,525,328 A | 6/1985 | Bredeweg |
| 4,608,859 A | 9/1986 | Rockley |
| 4,774,831 A | 10/1988 | Nordin |
| 4,797,906 A | 1/1989 | Smith |

(Continued)

FOREIGN PATENT DOCUMENTS

| | | |
|---|---|---|
| BR | 1120190119442 | 4/2023 |
| CA | 2068012 A1 | 12/1992 |

(Continued)

OTHER PUBLICATIONS

International Search Report and Written Opinion based on PCT/US2020/013261 dated Jun. 5, 2020.

(Continued)

*Primary Examiner* — Robert R Raevis
(74) *Attorney, Agent, or Firm* — Len S. Smith; Julie E. Kurzrok; Transformative Legal LLC.

(57) ABSTRACT

Provided herein are new methods of analyzing release-resistant water in materials, such as geologic materials. The methods of the invention typically comprise removal of extraneous water, e.g., by drying, preparing the material for the release of release-resistant water (e.g., by crushing the material, but typically not so greatly as to cause the release of fluid from hermetically sealed components, such as fluid inclusions), and then analyzing the amount of release-resistant water in the sample, either directly in-situ or by the additional step of extracting the release-resistant water and measuring the extraction. The invention also provides new devices and/or systems useful in the performance of such methods.

23 Claims, 6 Drawing Sheets

(56) References Cited

U.S. PATENT DOCUMENTS

| | | | |
|---|---|---|---|
| 4,960,567 | A | 10/1990 | Smith |
| 5,241,859 | A | 9/1993 | Smith |
| 5,286,651 | A | 2/1994 | Smith |
| 5,328,849 | A | 7/1994 | Smith |
| 5,341,859 | A | 8/1994 | Howseman, Jr. |
| 5,411,707 | A | 5/1995 | Hiatt |
| 5,416,024 | A | 5/1995 | Smith |
| 5,447,556 | A | 9/1995 | Pleil |
| 5,457,316 | A | 10/1995 | Cohen |
| 5,767,399 | A | 6/1998 | Smith |
| 6,541,272 | B1 | 4/2003 | Mitra |
| 6,661,000 | B2 | 12/2003 | Smith |
| 6,743,397 | B1 | 6/2004 | Zesiger |
| 7,150,184 | B1 | 12/2006 | Scott et al. |
| 7,210,342 | B1 | 5/2007 | Sterner |
| 7,354,768 | B1 | 4/2008 | Scott |
| 7,395,691 | B2 | 7/2008 | Sterner |
| 8,256,282 | B2 | 9/2012 | Schlachter |
| 8,536,524 | B2 | 9/2013 | Pomerantz |
| 2001/0015093 | A1 | 8/2001 | Kempe |
| 2002/0194896 | A1 | 12/2002 | Stolper |
| 2004/0099804 | A1 | 5/2004 | Liu |
| 2005/0109207 | A1 | 5/2005 | Olander |
| 2005/0194134 | A1 | 9/2005 | McGregor |
| 2006/0000110 | A1 | 1/2006 | Aisenberg et al. |
| 2010/0277724 | A1 | 11/2010 | Bounouar |
| 2011/0305309 | A1 | 12/2011 | Brown |
| 2012/0167786 | A1 | 7/2012 | Laugharn, Jr. |
| 2012/0186331 | A1 | 7/2012 | Tipler |
| 2014/0026638 | A1 | 1/2014 | Bowers, II |
| 2014/0104615 | A1 | 4/2014 | Kaneko et al. |
| 2014/0220700 | A1 | 8/2014 | Alexander |
| 2014/0283580 | A1 | 9/2014 | Rouchon |
| 2015/0123670 | A1 | 5/2015 | Robbat, Jr. |
| 2015/0155150 | A1 | 6/2015 | Bateman |
| 2015/0167052 | A1 | 6/2015 | Griffin |
| 2015/0346179 | A1 | 12/2015 | Pillot |
| 2016/0222781 | A1 | 8/2016 | Lawson |
| 2018/0195383 | A1 | 7/2018 | Smith |
| 2018/0306031 | A1 | 10/2018 | Smith |

FOREIGN PATENT DOCUMENTS

| | | | |
|---|---|---|---|
| CN | 1609586 | A | 4/2005 |
| CN | 201740685 | U | 2/2011 |
| CN | 104407089 | A | 3/2015 |
| CN | 105606686 | A * | 5/2016 |
| EP | 0414564 | A2 | 2/1991 |
| WO | WO2003050844 | A1 | 6/2003 |
| WO | WO2015050832 | A1 | 4/2015 |
| WO | WO2016186689 | A1 | 11/2016 |

OTHER PUBLICATIONS

International Search Report based on PCT/US2020/055436 dated Feb. 2, 2021.
Non-Final Office Action on May 17, 2018 for U.S. Appl. No. 15/908,760.
Extended European Search Report on Jul. 30, 2020 for EP17880886.1.
Indian Examination Report on May 16, 2021 for IN201917022180.2.
International Search Report on Apr. 6, 2018 for PCT/US2017/065921.
Jorge et al. "Analysis of Volatiles in Fluid Inclusion by Direction online Crushing Mass Spectrometry." Journal of Brazilian Chem Society 22.3, 2011: 43-455, p. 445, vol. 1 [online]. http://www.scielo.br/pdf/jbchs/v22n3/v22n3a05.ped Published Oct. 19, 2010.
Mazidi et al. "Measurement of Uniaxial Compressive Strength of Rocks Using Reconstructed Cores from Rock Cuttings." Journal of Petroleum Science and Engineering 86-87 (Mar. 2012): 39-43.
McCarthy et al. "Basic Petroleum Geochemistry for Source Rock Evaluation." Oilfield Review, 23.2, Summer 2011.
Non-Final Office Action on Oct. 9, 2018 for U.S. Appl. No. 16/019,523.
Final Office Action on May 2, 2019 for U.S. Appl. No. 16/019,523.
European Examination Report on Feb. 24, 2023 for EP17880886.1.
Russian Office Action on Aug. 19, 2020 for EA201991461.
SMITH_BR1120190119442B1_PD230425_SMITMICH20230425FRPAT01.
Non-Final Office Action on Oct. 9, 2018 for U.S. Appl. No. 16/019,529.
International Search Report and Written Opinion on Aug. 5, 2019 for PCT/US2019/22362.

* cited by examiner

ANALYSIS OF RELEASE-RESISTANT WATER IN MATERIALS AND RELATED DEVICES AND METHODS

CROSS-REFERENCE TO RELATED APPLICATIONS

This application is a continuation-in-part of PCT Application Number PCT/US20/13261, filed Jan. 12, 2020, entitled, "Analysis of Release-Resistant Water in Materials and Related Devices and Methods", which claims priority to U.S. Provisional Patent Application 62/791,879, filed Jan. 13, 2019, also entitled, "Analysis of Release-Resistant Water in Materials and Related Devices and Methods". This application claims the benefit of priority to, and incorporates by reference the entirety of, these above-referenced priority applications.

FIELD OF THE INVENTION

This invention relates to the evaluation of materials, such as samples of geologic materials, for example petroleum drill cuttings, through extracting certain kinds of water from such materials, measuring such extracted water, and using such information to evaluate the material and related material, such as characteristics of a petroleum drilling site.

BACKGROUND OF THE INVENTION

The analysis of materials is important in a variety of fields, especially in petroleum exploration and/or production. Oil and gas pay zones are routinely identified and mapped in petroleum exploration and production.

Wire line logs, especially resistivity logs, have been traditionally used to identify and map oil and gas accumulations, and are still frequently used today. Resistivity logs, however, are sometimes unable to locate pay zones in areas associated with certain conditions, which are characterized in the art as "low visibility pays." Low visibility pays can include areas such as freshwater basins in which the water legs have high resistivity or sandstone reservoirs having clay coatings around sand grains where there is low resistivity in the pay zone. In addition to their failure to operate properly in low visibility plays, resistivity logs are cost prohibitive for many wells, such as horizontal wells, which are increasingly important in modern petroleum production.

Fluid inclusion analysis of petroleum drill cuttings has been proposed as an alternative method of analyzing the contents of geologic formations, however, we now know that this method, which I helped to pioneer, is limited in its usefulness. While the results from fluid inclusion analysis can provide information about the fluid composition; temperature and pressure at which a material was formed; and what it can contain, the content of the inclusion often does not match the present-day fluids in the geologic formation and is of limited utility for identifying and mapping present oil and gas pay zones.

My earlier invention, described in U.S. Patent Application 2018/0306031 (referred to herein as "the '031 application"), discloses the extraction and analysis of volatile hydrocarbons and other organic compounds which can be extracted from geologic materials by the application of certain forces, such as relatively gentle vacuum pressure, to such materials, such as petroleum cuttings, by devices including cryogenic mass spectrometry devices that typically also include means for crushing samples. The analysis of the hydrocarbons and organic compounds of my prior invention produces relevant information about the geologic material associated with the petroleum cuttings, for example. One of the targets of that method is "oil saturated water", which refers to water containing oil-indicating organic compounds and organic acids. However, neither this invention, nor any other of my earlier work, included the use of water per se as an analyte in the analysis of materials, such as the identification of oil or gas pay zones.

In fact, prior to my invention described herein, it was believed by me and others in the field that water was too abundant of a substance and would not provide any useful value as an analyte in the analysis of materials, such as petroleum cuttings. It was also a concern that material-associated water could not be accurately measured by analytical methods used in analysis of oil-related materials, such as mass spectrometry.

PRINCIPLES OF CONSTRUCTION

The following principles should be considered in understanding this disclosure.

All references, including publications, patent applications, and patents, cited herein, including the patents and patent applications cited above, are hereby incorporated by reference to the same extent as if each reference were individually and specifically indicated to be incorporated by reference and were set forth in its entirety herein. Unless clearly contradicted by context or explicit statement, the disclosure of these applications (e.g., the analytical methods and devices described therein) can be combined with the teachings provided herein to provide additional useful aspects of this invention. This is particularly true of the devices of the '031 application, which can be used in the performance of the methods described herein, and the methods of the '031 application, which can be used to complement the methods described herein. The citation and incorporation of patent documents herein is done for convenience only and does not reflect any view of the validity, patentability, and/or enforceability of such patent documents.

All headings and sub-headings are used herein for convenience only and should not be construed as limiting the invention in any way. The use of the terms "a" and "an" and "the" and similar referents in the context of describing the invention are to be construed to cover both the singular and the plural, unless otherwise indicated herein or clearly contradicted by context. Use of the term "or" herein is not meant to imply that alternatives are mutually exclusive unless clearly stated or clearly contradicted by context. Thus, in this application, the use of "or" means "and/or" unless expressly stated or understood by one skilled in the art. In the context of a multiple dependent claim or a multiply dependent embodiment or aspect in a set or list of aspects/embodiments, the use of "or" refers back to more than one preceding independent or dependent claim. Lists of elements linked by the term "and" (e.g., A, B, and C) are to be interpreted as providing support for any one of the list, combination of the list, or all members of the list, unless it is clear from context that all members of the list are intended to be required in all cases.

The inclusion of "(s)" after an element or a step indicates that $\geq 1$ of such an element is present, step performed, and the like. E.g., "element(s)" means both 1 element or $\geq 2$ elements, with the understanding that each thereof is an independent aspect of the invention.

Recitation of ranges of values herein are merely intended to serve as a shorthand method of referring individually to each separate value falling within the range within an order of magnitude of the order of the range (e.g., a range of 1-2 is to be interpreted as providing support for 1.1, 1.2, 1.3, . . . and 1.9; a range of 10-20 is to be interpreted as providing support for 11, 12, 13, . . . and 19), unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate— e.g., disclosure of "about 10" is to be understood as also providing support for 10 exactly). Terms of approximation, such as "about" are used herein where measurements are understood to vary due to measurement issues or variability in measurements of large sets of samples, such as results of studies involving dozens, hundreds, or thousands of data points. The scope of such terms will depend on the context of the element at issue and the understanding of those skilled in the art. In the absence of such guidance in the art or through relevant disclosure, teachings, or examples provided herein, "about" should be understood as meaning +/−10% of the indicated value(s) (e.g., about 1 will mean 0.9-1.1 and about 10 will mean 9-11).

All methods described herein can be performed in any suitable order unless otherwise indicated herein or otherwise clearly contradicted by context. Unless clearly indicated or contradicted by context the elements of a device, composition, or method disclosed herein can be constructed, formulated, or executed in any suitable manner and compositions and devices can be made by any suitable method. Unless otherwise explicitly stated or clearly contradicted by context, any combination of the various elements, steps, components, and/or features of the aspects of the invention described herein, in all possible variations thereof, is to be considered encompassed by the invention.

The use of any and all examples, or exemplary language (e.g., "such as") provided herein, is intended merely to better illuminate the invention, and does not pose a limitation on the scope of the invention unless otherwise indicated. No language in the specification should be construed as indicating any element is essential to the practice of the invention unless as much is explicitly stated. The breadth and scope of the present invention should not be limited by any such exemplary embodiments or examples.

The description herein of any aspect or embodiment of the invention using inclusive terms such as "comprising", "having," "including," or "containing" with reference to a component, element, part, etc. in a composition, device, collection, and the like, should be interpreted, whether explicitly stated or not, as simultaneously providing support for a corresponding embodiment of the invention characterized in that the composition, device, or collection, to the extent not excluded by context or clear dictates of the disclosure, wherein the device or composition "consists of", "consists essentially of", "substantially comprises", "predominately comprises" and "substantially consists of" the referenced element, component, or part. Thus, for example, a composition described herein as comprising a particular element should be understood as also simultaneously describing a composition consisting of that element, predominately comprising that element, and substantially consisting of that element, unless otherwise stated or clearly contradicted by context.

The phrase "predominately comprises" means that more than one half (i.e., more than 50%) of the composition-at-issue, collection-at-issue, or device-at-issue, and the like, is made up of the referenced component or element. Unless clearly indicated the percentage of the element, feature, or component, should be understood as providing support for weight concentration, unit (e.g., molecular) concentration, and/or volumetric concentration. Corresponding phrases such as "is predominately comprised of" will be interpreted in the same manner.

"Substantially comprises" means that at least about 1% of the referenced composition (of the number of parts or molecules, weight of the composition, volume, and/or other element-to-element basis) is made up of the referenced element, component, or the like.

"Substantially consists of" means at least about 95% of the composition-at-issue or device-at-issue is made up of the referenced factor, component, part, or element.

"Substantially all" means at least about 98% and typically will mean at least about 99% or even at least about 99.9% (all three values are to be considered to be disclosed when the term is used). Thus, for example, a composition wherein substantially all of a material is removed means that at least about 98%, at least about 99%, or at least about 99.9% of the material-at-issue is removed from the composition. A composition wherein substantially all of the composition is composed of a component means at least about 98%, usually at least about 99%, and often even at least about 99.9% of the composition is made up of that component.

"Significant" and "significantly" mean results/characteristics that are statistically significant using $\geq 1$ appropriate test(s)/trial(s) in the given context (e.g., $p \leq 0.05/0.01$). "Detectable" means measurably present/different using known detection tools/techniques. The acronym "DOS" (or "DoS") means "detectable(ly) or significant(ly)."

The description of the specific embodiments provided herein will reveal the general nature of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

SUMMARY OF THE INVENTION

This section provides a summary of select aspects of the invention to illustrate the nature of the invention. However, as additional aspects are provided elsewhere in this disclosure, this Summary should not be interpreted as limiting the scope of the invention.

In aspects, the invention described herein provides a method for analyzing the amount of release-resistant water associated with a material comprising (a) placing a material in an enclosure such that the material is isolated from the environment; (b) removing substantially all of the extraneous water associated with the material, (c) removing substantially all of the released extraneous water from the enclosure; (d) applying an extracting force to the sample of material in the enclosure, wherein the extracting force is capable of causing the release of a detectable amount release-resistant water from the material if present, and (e)

measuring the amount of release-resistant water released from the performance of step (d). In aspects, step (e) comprises measuring the release-resistant water by application of a humidity meter, measurement of the difference of mass in the media before and after application of removal/extraction, use of a capacitance manometer, or a combination of any or all thereof. In aspects, the invention provides a method wherein the release-resistant water is the only water measured in the analysis. In aspects, the invention further provides a method wherein the step of removing the extraneous water comprises application of one or more initial forces that causes the release of a first gas from the material, wherein the one or more initial forces are capable of causing substantially all extraneous water, if present, to evaporate, and the method comprises removing the first gas, not incorporating such a first gas in subsequent analysis. In certain aspects, the one or more initial forces comprises application of a vacuum at a specific pressure and temperature applied to the material to remove substantially all the extraneous water while leaving a detectable amount of release-resistant water in the material. In aspects, all water removed in efforts to remove extraneous water is discarded and is not considered in the analysis.

In additional aspects, the invention provides a method for analyzing a material containing or potentially containing release-resistant water comprising: (a) removing at least about 99% of any water associated with the material that is removable from the material by subjecting the material to a temperature of at least about 100 degrees C. water at normal atmospheric pressure ("extraneous water") from the material to obtain extraneous water-free material; (b) applying an extraction force to the extraneous water-free material to release a detectable amount of extractable water that contained in the material after performing step (a) ("release-resistant water"), (c) measuring an amount of release-resistant water released from the material, and (d) using the measurement of the amount of release-resistant water to assess the characteristics of the material. In certain aspects, the method is repeated two or more times using two or more different materials using the same methods or methods of substantially similar efficacy for the removal of the extraneous water and extraction of the release-resistant water and substantially identical methods of measuring the release-resistant water. According to aspects, the material predominately is composed of rock, such as a sample of rock from a geologic site such as a petroleum well. In aspects, the material is petroleum drill cuttings.

In further embodiments, the invention provides a method such as any of the methods described above, wherein the method is performed on at least about 10 samples, in aspects about 500 or more samples, such as 1000 samples or more, obtained from different parts of a geological site such as a petroleum well, wherein the different parts of the geological site are, e.g., separated from each other in at least one dimension by at least about 30-about 300 feet, wherein the amount of release-resistant water in the material is indicative of the location of petroleum deposits in different areas of the geological site, e.g., petroleum well. In certain aspects, samples can be petroleum cuttings obtained from a low visibility play, such as on samples obtained from a freshwater site. In aspects, the invention provides a method performed on at least two petroleum drill cuttings obtained from a horizontal petroleum well. In aspects, the methods provided by the invention such as the methods summarized in this section are performed within less than about 5 minutes, and the method is performed on cuttings that are less than about 20 minutes old, e.g., less than about 5 minutes old or less than about 1 minute old (with respect to when such cutting reached the surface), such that the results of the analysis can be used to inform real time or near real time direction (steering) of the drilling operation.

In certain other aspects, the invention provides a method for analyzing a material containing release-resistant water comprising: (a) removing at least about 99% of any water associated with the material that is removable from the material by subjecting the material to a temperature of at least about 100 degrees C. water at normal atmospheric pressure ("extraneous water") from the material to obtain extraneous water-free material; (b) measuring an amount of remaining water remaining in the material ("release-resistant water") without extracting the release-resistant water, and (c) using the measurement of the amount of release-resistant water to assess the characteristics of the material. In aspects, step (b) of such a method comprises measuring water in the material in-situ.

According to still additional aspects, the invention provides methods of repeatedly analyzing material from different parts of a geologic site or formation, wherein the relative amounts of release-resistant water measured in each cycle from each sample is used to generate a map of one or more properties of the geological area, such as a geological site, derived from the measurements of release-resistant water. In certain aspects, the geological site is a petroleum well.

In additional facets, the method provides a system for analyzing release-resistant water in materials comprising: (a) a collection component capable of capturing samples and delivering samples into an enclosed analytical device; (b) a washing component configured to wash delivered samples in an average time of about 1 minute or less; (c) a drying component capable of removing extraneous water from washed samples in an average time of about 2 minutes or less; and (d) an enclosed device comprising, (i) a sorting component for sorting samples from one another, (ii) a crushing component configured to crush the samples in an average time of about 1 minute or less, and (iii) an analytical component capable of analyzing the amount of release-resistant water in the enclosure. In aspects, the enclosed device further comprises (iv) an extraction component capable of exerting a force on the samples capable of extracting an analyzable amount of release-resistant water. In aspects, the release-resistant water is the only water measured in the analysis. In aspects, the invention provides a system wherein the extraction component comprises both a heating component and a vacuum component, which can work independently and/or in concert to extract release-resistant water from the samples. In aspects, the analytical component capable of analyzing the amount of release-resistant water in the enclosure is a capacitance manometer.

In aspects, known equivalents of the techniques/steps described herein for performing such methods are used. E.g., in one aspect the invention provides a method of analyzing the release resistant water content of a material comprising (a) providing a material, (b) optionally applying a step for removing extraneous water from the material (e.g., by manual drying, heat drying, or other method described herein or known equivalents of such methods), (b) optionally applying a step for extracting release-resistant water from the material (e.g., by applying a vacuum pressure such as described herein or any force or combination of forces that would be recognized as equivalent thereto in the art for the extraction of such fluid from the material), and (c) applying a step for measuring release resistant water in the material (e.g., using capacitance manometry, any other method described herein, or equivalents known in the art for measuring such fluids (in situ, after extraction, or both). As exemplified by the preceding sentence, the various steps described herein can also be characterized as "steps for" performing the various function associated with each step.

BRIEF DESCRIPTION OF THE DRAWINGS/FIGURES

Figure 6A:
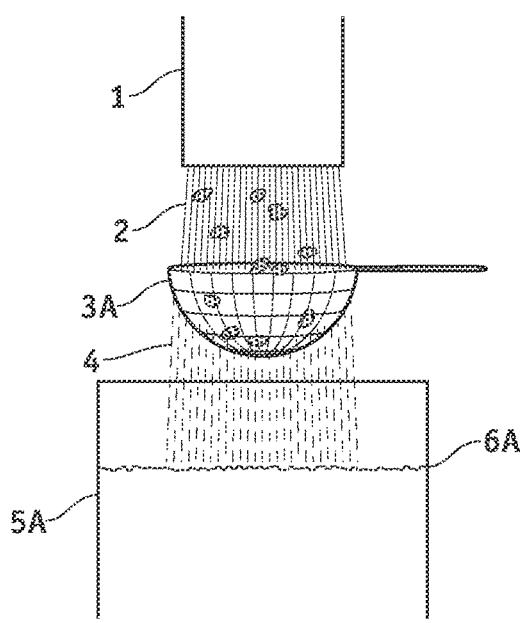
Figure 6B:
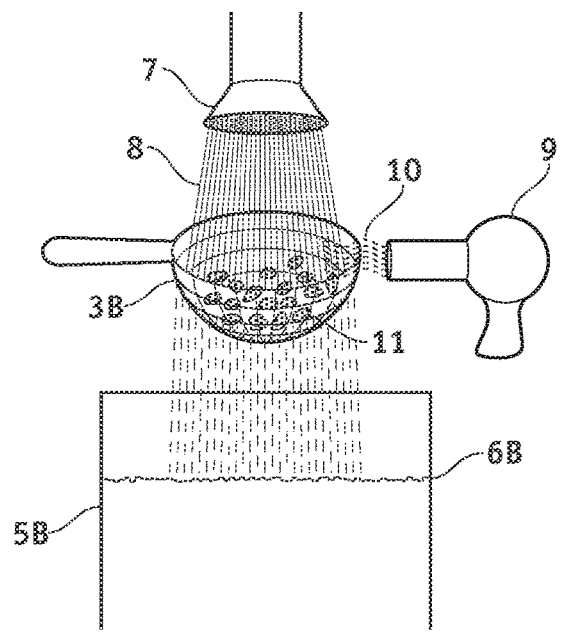
Figure 6C:
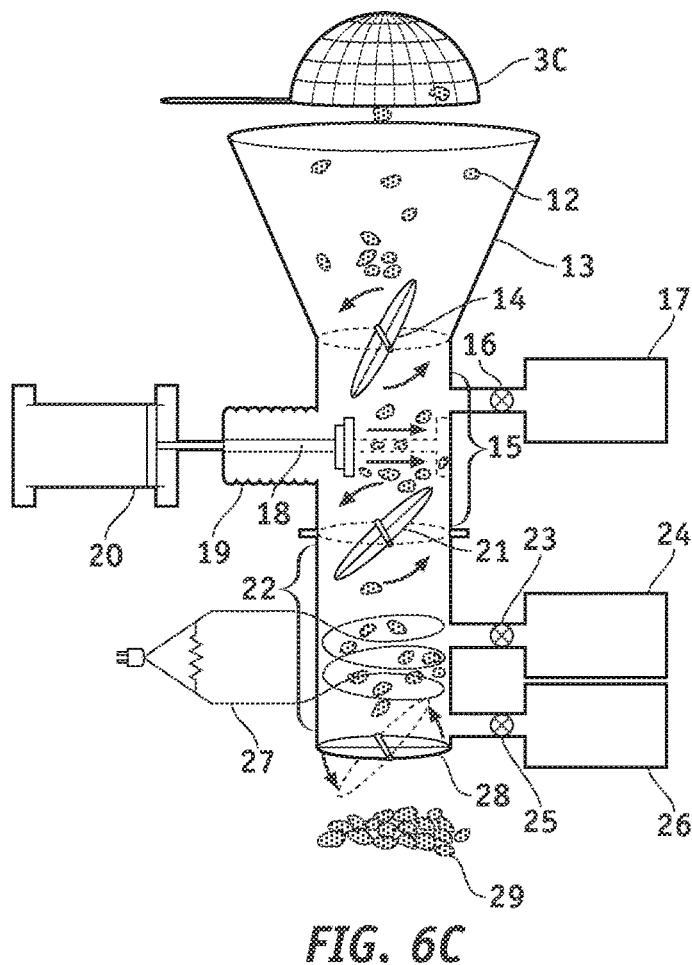

FIGS. 6A, 6B, and 6C provide an illustration of aspects of an exemplary device/system that can be used in performance of the methods of the invention at a petroleum drilling site. FIGS. 6A and 6B specifically illustrate the application of components of such a device/system in the removal of extraneous water from (drying of) samples of material and FIG. 6C illustrates the remaining parts of such a device/system being applied to dried samples.

DETAILED DESCRIPTION OF THE INVENTION

The invention provided herein provides new methods as well as devices/systems that not only address the limitations of the above-described prior technologies and inventions but that also greatly expand on such prior methods/devices/systems in terms of the applicability to sites/areas of interest, including but not limited to horizontal and low visibility pay zone petroleum wells. These and other advantages of the invention, as well as additional inventive features, will be apparent from the description of the invention provided herein.

Specifically provided herein are methods for analyzing release-resistant (or "arrested") water contained in or otherwise associated with materials, such as samples from a geologic site (e.g., petroleum drill cuttings from a petroleum well) and devices for performing such methods.

Materials analyzed in the methods of this invention are typically predominantly solid and usually nearly entirely solid in nature, but the material will usually also comprise and/or be associated with some amount of water (typically in the form of aqueous material comprising other substances) and possibly other liquids associated with (e.g., coating) or contained in the material.

Geological Sample Locations and Materials

Typically, methods of the invention are performed on geological samples (e.g., samples of rock or other geologic samples collected from various geological locations). Herein, a "material" can be any suitably analyzable material that contains or can potentially contain release resistant water (as described in more detail elsewhere). In typical aspects, a material is, or materials are, geological sample(s), such as a sample of rock, e.g., a collection of petroleum drill cuttings. A sample can be collected from any number of geological locations. In aspects, samples are collected from one site (sites are described below). In aspects, samples can be obtained from any suitable location within one or more sites. In other aspects, as exemplified herein, samples are obtained from multiple sites. Typically, multiple samples collected from one or more sites and from one or more locations within such one or more sites are used in the methods provided by the invention. With a site, samples can be obtained from any suitable number of locations. In aspects, samples are obtained from at least about 10 (e.g., at least about 25, at least about 50, at least about 70, or at least about 100) separate locations within a site, within an area containing multiple sites, within a geological area, such as a geological formation, from any other suitable geologic unit, or from some combination thereof. In aspects, any suitable number of samples can be provided (or collected) in performance of such multi-sample methods.

Multiple terms may be used herein to describe geologic locations or geological features from which samples can be collected and analyzed using the methods and systems provided by the invention. Herein a "formation" is understood in the art to mean an identified area of strata having similar lithology. In some cases, a formation also may be defined by other characteristics, such as biostratigraphic characteristics, chemostratigraphic characteristics, or both, and sometimes such characterizations of a formation are used interchangeably (e.g., the Meramec Shale Formation is often referred to as the Mississippian Formation, reflecting the period in which the rock was deposited). Typically, a formation is a series of strata/beds that is distinct from other beds above and below and is thick enough to be shown on the geological maps that are widely used within the area in question. Formations can be divided into sub-formations or "members" based on such characteristics. Formations also can be grouped together into "groups." Both "groups" and "members" are commonly used terms of art. For example, a formation that includes both shale and sandstone might be divided into members, each of which is either shale or sandstone. In some areas, where more detail is needed, members may even be further divided into beds. A "group" typically represents a series of rocks deposited within a single basin (or a series of related and adjacent basins) over a geologic period (e.g., a few million to a few tens of millions of years). "Basins" are large-scale structural formation of rock strata formed by tectonic warping. The Permian Basin in Texas (comprising Wolfcamp, Cline shale, Strawn, and Atoka formations) is a well-studied example of a basin. Basins can include "sub-basins" (e.g., the Permian comprises the Delaware Basin, Midland Basin, and Central Basin Platform). The oil rich Wolfcamp Shale Formation is present in all three sub-basins. This fact (and terminology) demonstrates that the line between formations and groups is not always clear and that aspects described here with respect to one implicitly provide support for the other and vice versa. The term "geologic unit" is used here to refer to any discrete geologic area (a basin, group, formation, member, bed, area, or site).

In petroleum production the term "play" is used to indicate a region defined by a group of oil fields (each comprising many wells/sites) that generally share the same set of geological circumstances (e.g., formations present). Plays can be divided into "regions" or "areas" comprising two or more (often several) sites, potential sites, or both.

A typical "site" is a petroleum well or an area of prospective petroleum drilling within an area or play. A site will comprise many distinct locations that can be characterized based on vertical depth and lateral/lengthwise distance. Typically, samples are provided from (or collected from) more than 10 separate locations, such as at least about 20, at least about 30, at least about 40, at least about 50, at least about 65, at least about 75, or at least about 100 locations. In aspects, samples are provided from more than 100 locations, such as at least about 125, at least about 150, at least about 200, at least about 250, or more different locations in a site or related site(s). In aspects related sites share common geological features, e.g., they reside within a shared geological unit (e.g., a shared basin, group, formation, member, bed, or area) such as, e.g., they may reside within a shared defined geological area such as a play.

Site(s) can be any suitable type of site(s). In aspects, a site is an active petroleum well, an old dormant well, or an area of petroleum exploration (a potential well site). Wells can be traditional vertical wells, later wells, or comprise aspects of both types of wells. In aspects, methods comprise application of such methods to lateral wells. In aspects, methods comprise application to existing lateral wells to assist in analysis of further lateral drilling, fracking in the later well, or a combination thereof. In aspects, the methods are applied to determine if drilling should be performed in a site, parts/areas of a site, or both. In aspects, the site(s) from which samples are obtained comprise or are expected to comprise, based on other analytical methods/indicators, one or more low visibility plays. In aspects, site(s) are site(s) for which other methods or indicators have provided some suggestion of the presence of petroleum (e.g., where confirmation of such signal(s)/indicator(s) are desired). In aspects, samples collected from different locations within a single site can define characteristics of the different locations within the single site, such as higher or lower petroleum producing locations within the site, or higher or lower potential productivity of different locations within a single site.

Types of Material-Associated Water

Water associated with a material to be analyzed by the methods described herein, such as a geologic material or a sample thereof (e.g., a petroleum drill cutting or core sample) can be characterized as "extraneous water" (which is also sometimes called "free water") or "release-resistant water" (which is also sometimes referred to herein as "arrested" water). As used herein, "extraneous water" can be considered any water associated with a material that is not release-resistant. "Extraneous water" can, and typically does, comprise both formation water and other water, such as process water, that can be, or could be, easily extractable. While extraneous water can come from different sources and have different characteristics, any such separation is inconsequential to the invention described herein. As such, "extraneous water" is typically referred to herein as a single entity.

Free water/extraneous water is significantly easier to remove from material than release-resistant water. In one aspect, "extraneous water" means water that is removable from a material, such as a sample of a geologic unit, in aspects such a unit being a geological site such as a petroleum well and such samples being, e.g., drill cutting(s)), by the application of one or more forces/conditions (extraneous water removal force or "EWRF") that is at least about as effective (in terms of removal of such water from the material) as removing water from the material by boiling the water under typical atmospheric conditions (e.g., exposing the material to a temperature of at least about 100 degree C. temperature, and typically a temperature slightly above 100 degrees C., such as about 105-125 degrees C., e.g., about 110 degrees C.) for a period of time sufficient to convert any such liquid water to water vapor, but which force is not strong enough to cause the release of a significant amount of release-resistant water (e.g., is not able to cause the release of more than about 10%, more than about 7.5%, more than about 5%, more than about 3%, more than about 2%, or more than about 1%, e.g., more than about 0.5% or more than about 0.1% release-resistant water from the material).

The process of boiling water, especially most, substantially all, or all of the water in a material, will vary with temperature, pressure, the amount of water present, time, and volume, if applicable, such as the size of any container that the sample or material is placed in, according to principles known in the field. As such, different conditions can, in aspects, be effective for removal of extraneous water by application of boiling (in terms of temperature, condition, and volume, as would be understood in the art).

The removal of extraneous water also is not limited to the application of vacuum and/or temperature. Other techniques, such as physical or chemical water removal, also or alternatively can be used in the removal of extraneous water from the material (the terms material and sample should be considered to provide support for one another herein, even when each is not explicitly stated, except where clearly contradicted by context or express statement).

In one embodiment, the removal of extraneous water from the material comprises the application of one or more physical forces to the material to remove some, typically most, and often at least about 80%, at least about 85%, at least about 90%, or even substantially all of the extraneous water is removed by application of such a physical removal step. A physical removal step can include drying by contact with a physical media, such as an absorbent material, by spin drying, or by a combination thereof. Removal of extraneous water can also or alternatively be performed by application of temperature and/or application of a vacuum pressure, as exemplified below, or a combination of any of these methods with any other suitable drying method, including chemical drying as discussed further herein and in the '031 application. Such physical steps often have a high level of efficacy against most of the extraneous water associated with a material, and such physically removable water is often removed very quickly, e.g., within a period of about 5 minutes or less, often about 2 minutes or less, such as about 1.5 minutes or less, about 1 minute or less, about 0.75 minutes or less, or about 0.5 minutes or less.

Thus, with respect to the boiling standard discussed above this is typically applied in connection with the removal of a portion of the total extraneous water associated with a sample that remains after application of physical removal. In such cases, the amount of extraneous water left as water associated with the sample can, in aspects, be small and the amount of time required to remove most, substantially all, or all of such remaining extraneous water from the material cancan be relatively limited. For example, application of a temperature of about 100 degrees C. to about 130 degrees C., such as about 100 degrees C. to about 125 degrees C., e.g., about 100 degrees C. to about 120 degrees C., e.g., about 100-130 degrees C. (e.g., about 100-about 125 degrees C., about 100-about 120 degrees C., about 100-about 115 degrees C., about 100-113 degrees C., about 100-about 110 degrees C., about 100-about 105 degrees C., or about 100-about 103 degrees C., such as about 101-about 125 degrees C., about 101-about 115 degrees C., or about 101-about 113 degrees C.), at about atmospheric pressure, will be able to remove most, substantially all, or all of such extraneous water within a period of about 0.25 minutes to about 10 minutes, typically about 0.5-about 7 minutes, such as about 0.5-about 5 minutes, about 0.5-about 4 minutes, about 0.5-about 3 minutes, about 0.5-about 2.5 minutes, or about 0.5-about 2 minutes, such as about 0.25 minute-about 1.5 minutes or about 0.2 minutes to about 2 minutes). In cases where there is no physical removal or very limited amount of physical removal of extraneous water, the amount of time required to boil most, substantially all, or all of the extraneous water can, in aspects, be longer, such as about 5-30 minutes, about 5-20 minutes, or about 5-15 minutes).

As reflected above, the force(s) used in the removal of extraneous water can be greater than the minimum required for boiling or other form of removal of the extraneous water, so long as such forces do not cause significant release of release-resistant water and thereby cause the mixing of release-resistant water and extraneous water. For example, application of a vacuum at about 20 millibars can be used in a container such as those described in the '031 application, at ordinary room temperatures (e.g., about 20-25 C, typically about 22-24 C), for a period of at least about 5 minutes, such as about 5-10 minutes. Within a container of about this size (about 0.25-inch diameter and about 3.25 inches long, typically containing about 300-500 microliters of material, such as about 400 microliters of material), such conditions will cause extraneous water to boil off of a typical petroleum cutting sample within such a period. Typically, so long as the force applied to removed extraneous water does not also cause extraction of release-resistant water in a way that the two types of water are mixed, any application of force for the removal of extraneous water will be suitable.

A number of suitable forces, or a suitable combination of two or more thereof, can be used to remove extraneous water and the above-described heating and vacuum methods are only intended to provide a standard in terms of efficacy of water removal. Any suitable method or combination of methods can be used for the removal of extraneous water so long as the result is the removal of most, substantially all, or essentially all (at least about 99%, at least about 99.5%, at least about 99.9%) of the extraneous water, without significant release of release-resistant water (e.g., no more than 5% of the release-resistant water in the material, no more than about 2.5% of the release-resistant water in the material, or no more than about 1% of the release-resistant water in the material is released due to the application of the EWRF).

As noted elsewhere herein, with respect to geologic materials, extraneous water typically includes water associated with a material or a sample due to placement in fissures and cracks in the material or that is associated with the surface of the material. Thus, extraneous water also includes formation water that is not "release-resistant" in the rocks, rock fragments, or other materials analyzed in the practice of the inventive method, such as petroleum drill cuttings.

However, extraneous water also can include water used in a drilling process or process of forming or modifying the material or samples, such as in the case of petroleum drill cuttings. To illustrate, once non-release-resistant formation water enters the bulk volume of drilling mud, that water becomes part of the drilling mud and cannot be separated out of the mud as distinguishable from the other process water in the mud. As such, drilling mud that is a carrier for materials such as petroleum drilling cuttings will typically contain non-release-resistant formation water from all the sediment(s) which have resulted from drilling in the current well and can even contain non-release-resistant formation water from previous wells if the mud has been reused on multiple wells as is often the case. It is expected that such "process water" will typically be readily removed by physical means, whereas the extraneous formation water will, at least in some significant amount, remain associated with the material, after application of physical removal methods, though such extraneous water will still be readily extractable by boiling through application of heat or gentle vacuum pressure, as exemplified and described above. Such process water can also include water on material, such as cuttings, remaining from washing or rinsing the material, in processes in which a rinsing/washing step is included in the method or otherwise is associated with the processing of the material.

In aspects, any aliquot of water (including water vapor) or other volatile(s) extracted or removed from a material prior to the extraction and analysis of release-resistant water is discarded and not included in the analysis provided by the method(s) here. In aspects, extraneous water, e.g., water removed prior to the analysis of release-resistant water, is discarded, and not considered in the analysis. In aspects, release-resistant water is the only water analyzed as a part of the methods provided by the invention. In aspects, release-resistant water is the only analyte measured by methods provided by the invention. In aspects, release-resistant water is the only analyte measured by methods provided by the invention, but the results of release-resistant water analysis can be combined with results of other analytical methods, such as, e.g., volatiles analysis, to characterize a geological unit under study, such as, e.g., a geological site such as a petroleum well. In aspects, release-resistant water alone is measured by the method(s) provided by the invention and is sufficient alone to characterize the geological unit under study (e.g., is sufficient to identify pay zones within a petroleum well).

Accordingly, "release-resistant water" (which also sometimes called "resistant water," "arrested water," or "tight water" herein) is water or a predominately water (i.e., aqueous) composition that is closely associated with a material due to its physical relationship to the material or otherwise (e.g., water contained in microfractures, micropores, nanopores, or other structures and/or physically bound to the material due to tight pore size, capillary interactions, or other possible interactions). Because in the context of materials obtained from, e.g., various geological units such as sites within geologic formation(s), this water/aqueous fluid is predominately, and typically substantially entirely, made up of water that is present in a formation before coming to the surface, release-resistant water in such contexts forms a part of the "formation water" and is entirely or essentially entirely characterizable as "formation water," whereas often most of the extraneous water in such contexts will be process-associated water or other non-formation water.

In one respect, "release-resistant water" can be characterized as water associated with a sample or material, e.g., a petroleum drill cutting or core, after the removal of substantially all, essentially all, or all of the extraneous water associated with the sample or material (e.g., removal of at least about 90%, at least about 95%, at least about 97%, at least about 98%, at least about 99%, at least about 99.5%, or at least about 99.9% of the extraneous water associated with the material).

Release-resistant water is typically only extractable from the material upon the application of a force sufficient to cause the disassociation of the water from the material. While application of basic physical drying techniques, for example, will be able to remove a substantial amount of, and often most or even substantially all of the extraneous water associated with a material, such techniques will typically have little impact on release-resistant water, which will remain associated with the material. Thus, extraction of release-resistant water requires application of one or more forces (release-resistant water extraction force or "RRWEF") that is capable of extracting a measurable amount of release-resistant water from the material.

Using application of vacuum force as a standard, for example, "release-resistant water" herein can be characterized as water that will be released from a geologic sample, such as a petroleum cutting, by application of a vacuum at a pressure of about 3 millibars or less to the sample in a suitable container for capturing most of any release-resistant water extracted by application of the force (e.g., a container with a diameter of about 0.25 inches, a length of about 3.25 inches, and containing about 400 micrograms of sample), optionally after crushing the sample, at room temperature, for a period sufficient to remove a measurable amount of release-resistant water from the sample for analysis, typically at least about 5 minutes (e.g., at least about 6 minutes or at least about 7 minutes, such as about 7.5 minutes or about 5-10 minutes) or a substantially equivalent force (in terms of efficiency/efficacy of extraction of release-resistant water).

In other aspects, the force used to extract the release-resistant water from the sample cancan be equivalent to the application of even a stronger vacuum such as about 2.5 millibars or less, such as about 2.25 millibars or less, about 2 millibars or less, about 1.75 millibars or less, or about 1 millibars or less. In other aspects, the extraction force used to extract release-resistant water from the geologic material or sample thereof can be defined as a force substantially equivalent to a force defined by a range of vacuum pressures such as about 0.5 millibars-about 5 millibars, about 0.75-4.75 millibars, about 1 millibar-5 millibars, or about 1 millibar-about 4 millibars, about 1.75 millibars-about 3.75 millibars, about 1.5 millibars-about 4.5 millibars, or about 1.5 millibars-about 3.5 millibars. In still other facets, the time the extraction force is applied to the sample to extract release-resistant water also or alternatively is longer than about 2 minutes, such as at least about 5 minutes, at least about 6 minutes, or at least about 7 minutes, or a range thereof, such as about 4-about 8 minutes or about 4-about 10 minutes. As discussed above, the minimum effective vacuum pressure for extraction of release-resistant water and the minimum effective time for extraction of a measurable amount of such water will vary with conditions such as the amount of water presence, the nature of the material, temperature, pressure, and relevant volumes (container size, pore/micro-fissure sizes in the material, etc.).

Those of ordinary skill in the art will recognize that application of such a force to a material or a sample can cause release-resistant water to boil and in such contexts, it is through the vaporization of such release-resistant water that it can be extracted from the material or sample. The amount of vacuum pressure needed to cause such boiling (a vacuum extraction force) can vary with the size of the container in which the vacuum is applied and/or the temperature inside the container.

As noted, and as exemplified further herein, application of markedly weaker vacuum (characterized by a higher millibar measurement), such as application of a vacuum of about 20 millibars, under typical environmental conditions, can, in aspects, be sufficient to remove extraneous water from a sample, but typically will not be able to extract release-resistant water.

The extraction of release-resistant water is not, however, limited to the application of vacuum pressure, although application of vacuum pressure can be a convenient method for extracting release-resistant water from samples of geologic materials. In one embodiment, in addition to application of vacuum, a physical disruption of the sample, such as by crushing the sample, is also applied, to promote greater release of release-resistant water from the sample. In a particular aspect, the crushing step comprises crushing the sample in a crushable container that can be crushed without the release of volatile materials, examples of which containers and methods are exemplified in detail in the '031 application, incorporated herein by reference. In another embodiment, samples can also or alternatively be subject to a drying step prior to the application of vacuum at a release-resistant water extraction pressure or other release-resistant water extraction step.

It should be noted, however, that release-resistant water either does not include or includes only a very small amount of water that was originally contained hermetically sealed structures, such as unbroken fluid inclusions in petroleum samples. The amount of water from fluid inclusions, however, will typically be very limited in the extraneous water (typically making up less than about 50%, less than about 33%, less than about 20%, less than about 10%, less than about 5%, less than about 2%, or even less than about 1%, of the extraneous water removed in the drying step. Fluid from fluid inclusions typically also will make up an even smaller proportion of the water captured as release-resistant water (e.g., less than about 10%, less than about 5%, less than about 2.5%, less than about 1%, less than about 0.05%, less than about 0.01%, or less than about 0.001% of the release-resistant water). As noted elsewhere, release-resistant water will not include fluid hermetically sealed in fluid inclusions that have not been ruptured in the drilling process or the crushing process of the method. Thus, it will be clear to those of skill in the art that the methods provided herein are remarkably different from fluid inclusion analysis methods currently used in the art for characterizing geological units such as geological sites in petroleum exploration and production, although in some cases the methods provided herein can be performed in concert with such methods.

In one embodiment, the force applied to extract the release-resistant water is such that a measurable amount of release-resistant water can be extracted from the material within less than about 6 minutes, such as less than about 5 minutes, less than about 4 minutes, less than about 3 minutes, or less than about 2 minutes. In some embodiments, the RRWEF is great enough that a measurable amount of release-resistant water is extracted from the material in about 90 seconds or less, about 80 seconds or less, about 60 seconds or less).

In some embodiments, an upper limit on the application of the force can be established to ensure that other components of the material or sample that are desired to be maintained are maintained and/or that the sample or material is not damaged in a manner that interferes with the analysis of the release-resistant water. For example, in the context of cuttings, an upper limit might be set to avoid high temperatures and/or low pressures that would cause hydrous materials (e.g., gypsum, clays, and the like) to decompose and thus release water held in their crystalline structures, which might interfere with correct measurement of release-resistant water. In one embodiment, less than about 5% of any water present at any time in the method is attributable to such structural water, such as less than about 3% of any water, less than about 2% of any water, less than about 1% of any water, less than about 0.5% of any water, or less than about 0.1% of any water present in the method.

Like water in fluid inclusions, any such water in crystalline mineral forms within a material is not "extractable" and, as such, will generally not be considered to be "release-resistant water." However, the presence of small amounts of such mineral-associated water in the release-resistant water of a material or sample, as is the case with water from disrupted fluid inclusions (as discussed elsewhere herein), will typically not render the results of the method to be in error and, as such, will not change the fundamental nature of the sample's "release-resistant water." Accordingly, in some embodiments, release-resistant water can include small amounts of fluid inclusion water and/or mineral-associated water, e.g., less than about 5%, less than about 3%, less than about 2%, or less than about 1% (e.g., less than about 0.5%, less than about 0.25%, or less than about 0.1%) of the release-resistant water being made up of such fluid inclusion or mineral associated water, with mineral associated water likely making up very little, if even any detectable amount, of the release-resistant water aliquot (as also noted elsewhere herein).

The invention described herein provides various methods in which release-resistant water is measured and analyzed so as to provide information about the properties of a material, such as a rock sample, e.g., a petroleum cutting. As noted above, in many cases the method will require the step of removing extraneous water (e.g., process water, extraneous formation water, and/or water from washing the material).

In one exemplary embodiment, the invention provides a method for analyzing a material containing release-resistant water comprising: (a) removing at least about 95%, at least about 97%, at least about 98%, at least about 99%, at least about 99.5%, or even at least about 99.9% of any water associated with the material that is removable from the material by subjecting the material to a temperature of at least about 100 degrees C. water at normal atmospheric pressure ("extraneous water") from the material to obtain extraneous water-free material; (b) applying an extraction force to the extraneous water-free material to release a detectable amount of extractable water that contained in the material after performing step (a) ("release-resistant water"), (c) measuring an amount of release-resistant water released from the material, and (d) using the measurement of the amount of release-resistant water to assess the characteristics of the material. In alternative embodiments of the invention, the step of extracting release-resistant water is substituted with a method of measuring release-resistant water remaining the rock ("in-situ" or "in situ"). In a more particular exemplary embodiment, the invention described herein provides a method for analyzing release-resistant water that is associated with a material comprising the steps of (a) placing the material in an enclosure (e.g., a container configured for use in the method) such that the material is isolated from the environment; (b) removing substantially all of the free/extraneous water if present from the material (which typically will also entail removing substantially all of the released extraneous water from the enclosure); (c) applying a force to the material that is capable of causing the release of an analyzable amount of resistant water from the material; and (d) measuring the amount of release-resistant water released from the material. Methods of the invention can be used, e.g., to assess petroleum producing properties of a petroleum well site. In one embodiment the method is performed quickly (e.g., in less than about 7, less than about 6, less than about 5, or less than about 4 minutes) and the results of the method are used to guide the drilling of a well in a "real time" manner. The invention also provides various new devices and systems for carrying out such analytical methods.

Methods of the Invention

As noted above, the invention provided herein relates to and provides methods of identifying and analyzing (e.g., relatively quantifying) the amount of release-resistant water contained in materials, such as geologic materials, for example petroleum drill cuttings.

Certain materials can contain water that is "release-resistant" (or "release-resistant"). Such materials can, in aspects, have microfractures, micropores, nanopores, and similar structures and/or physiochemical characteristics/features that cause water and aqueous fluids to "tightly" associate with such materials, such that an amount of this water will remain associated with such materials even when the materials are subjected to drying in significant part.

In the case of geologic materials, such resistant water reflects an important part of formation water, i.e., water that is present in the rocks of the actual geological site (e.g., formation), under normal geologic conditions.

Petroleum cuttings are an important example of such a material as I have surprisingly found that the determination of resistant water in cuttings is indicative also of the presence of current day oil in the relevant location of the geological unit under investigation, meaning that the mapping of the relative amount of resistant water in cuttings from an area under study can also map oil deposits.

While not intending to be bound to any particular theory, I believe that small fractures can form during the petroleum drill process and capture such aqueous compositions, and tightly bind them due to capillary forces and/or other physiochemical associations.

Regardless of how resistant water is formed in materials, such as cuttings, such materials have now been demonstrated to be present in such materials, and, contrary to conventional belief in the field, water, particularly this class of water, can now be accurately analyzed, providing important information about the material, such as a relative measure of Sw in the case of petroleum drill cuttings.

Thus, in one aspect, the invention provides a method of measuring release-resistant water in a material and using the measurement of release-resistant water to characterize the material. In one embodiment the material is a geological unit such as a formation, basin, group, member, bed, area, site, or the like, or a geological material collected from a geological unit such as drill cuttings for core sample(s) from a petroleum well. In one aspect, the method is performed on numerous samples or different areas of a geologic unit (e.g., site) or larger material (e.g., a structure). In many aspects, the method will comprise a step of removing extraneous water so as to ensure an accurate measurement of release-resistant water. Release-resistant water can be characterized based on its resistance to extraction and/or removal methods that removal extraneous water, its presence in certain structures of the material (e.g., nanopores, micro-fissures, and the like), or both. Typically release-resistant water will include very little, if any, water from fluid inclusions and water generated from the decomposition of water-containing materials (structural water), as discussed elsewhere herein.

According to one exemplary embodiment the invention provides a method for analyzing a material containing release-resistant water comprising: (a) removing at least about 90%, at least about 95%, at least about 98%, at least about 99%, at least about 99.5%, at least about 99.9% or more of any extraneous water, which can be characterized as water associated with the material that is removable from the material by subjecting the material to a temperature of at least about 100 degrees C. water at normal atmospheric pressure ("extraneous water") from the material to obtain extraneous water-free material; (b) applying an extraction force to the extraneous water-free material to release a detectable amount of extractable water that contained in the material after performing step (a) (i.e., the "release-resistant water"), (c) measuring an amount of release-resistant water released from the material, and (d) using the measurement of the amount of release-resistant water to assess the characteristics of the material. In some embodiments, the material is enclosed before the extraction of at least some of the release-resistant water, e.g., by placement of the material into a container, which typically will be impermeable or substantially impermeable to water. In some cases, the entire method is performed in one or more enclosures/containers. In other embodiments, at least part of the method, typically at least part of the removal of extraneous water, is not performed in a container.

In some embodiments the type of extraneous water is limited to (i.e., more narrowly characterized/defined as) water that can be removed the material or type of material on application of at least about 100 degrees C., typically at least about 100 degrees C. to less than about 125 degrees C., such as less than about 115 degrees C., or less than about 110 degrees C. or less than about 105 degrees C., for a limited period of time, e.g., for less than about one hour, less than about 40 minutes, less than about 30 minutes, less than about 20 minutes, or less than about 15 minutes (in all cases at a typical atmospheric pressure, which includes those atmospheric pressures generally encountered at less than 12,000 feet elevation). It is understood that in cases of boiling water, prolonged exposure can in some cases result in superheating of the water, but this is not required for the removal of extraneous water (though such methods can, in aspects, be employed in the extraction of release-resistant water).

In embodiments, the steps of the above-described method, or any of the other methods described herein, will be repeated two or more times using two or more different materials, such as, for example, geologic samples, such as cuttings (well cuttings, such as petroleum well cuttings), obtained from two different locations of a geologic unit, e.g., a site, such as a petroleum well. Typically, a method comprising repeating the above-described steps will comprise using the same method(s) or method(s) of substantially similar efficacy for the removal of the extraneous water and/or extraction of the release-resistant water. Such repeated step methods will also typically comprise performing substantially identical steps/methods of measuring the release-resistant water from the two or more materials or samples that are tested in the method. Such methods may also use similar/same methods for analyzing such material based on measure release resistant water, but may also factor in other information such as patterns of data from the analysis of multiple materials, information about the materials, information about the materials in relationship to characteristics of the site (e.g., presence of fault(s), known history of petroleum presence/production/migration, measurements of related data from application of other methods, or any combination thereof).

Methods such as those described above can be performed on any suitable material(s), as discussed elsewhere herein. According to one embodiment, the material is at least about 10% composed of rock, is at least about t 25% composed of rock, is predominately/mostly composed of rock, is at least about 70% composed of rock, is at least about 85% composed of rock, is at least about 90% composed of rock, is at least about 95% composed of rock, or is at least about 98% composed of rock (e.g., is about 99% or about 100% composed of rock). Rock material can be sourced from any suitable location and have any suitable origin. Often the rock material will be directly obtained from a geologic area or geologic unit. In one embodiment, the geologic unit is an area associated with one or more petroleum drilling sites (for production and/or exploration, which wells can be active and/or inactive). In embodiments, the material will be a sample taken from a petroleum drill site, such as a core sample. In common embodiments, the material will be a petroleum drill cutting (and in methods in which multiple samples are tested, at least some, at least half, substantially all, or all the materials tested will be petroleum drill cuttings).

Methods of the invention in which extraneous water is present will often include a step of physical removal of extraneous water (e.g., removing at least about 75%, at least about 90%, at least about 95%, at least about 99%, or about 100% of any material-associated extraneous water). In embodiments, physical removal of extraneous water is sufficient in itself to prepare the material for extraction of release-resistant water (or, in in-situ methods, for directly analyzing the content of release-resistant water remaining in the material). In many embodiments, both physical removal of water and one or more applications of non-physical water removal forces/methods are employed. Physical removal methods are methods that do not include as a primary basis of water removal the use of heat or vacuum pressure. Thus, physical water removal methods can include application of positive pressure (e.g., blow drying), contact with absorbent materials (e.g., cloth drying), removing water through agitation or gravity (e.g., by rapidly spinning the material to shake water off the outer surface thereof), through contact with water absorbing chemicals (e.g., Drierite™), or through a combination of two or more of any of these methods/forces.

According to certain embodiments, most, substantially all, or all of the water removal methods are carried out at less than about 100 degrees. In such cases, the combination of physical methods and vacuum pressure can be employed to ensure that extraneous water removal is carried out at relatively lower temperatures. The vacuum force necessary to remove extraneous water will depend on the nature of the material, amount of water present, the enclosure (if any) in which the material is situated, the temperature, and other factors know in the art and/or discussed herein. In, for example, a cylindrical container with a diameter of about 0.25 inches and a length of about 3.25 inches, containing about 300-500 microliters of a rock sample (as a single rock or more likely as a collection of smaller rock fragments, such as PDC cuttings), applying a vacuum of about 20 millibars (e.g., about 15-30 millibars, about 17-25 millibars, about 18-23 millibars, or about 19-21 millibars) for a period about 5-15 minutes, such as about 6-12 minutes, such as about 7-10 minutes, e.g., about 7.5-9 minutes, at about room temperature (e.g., about 18-22 degrees C.) is typically sufficient to remove extraneous water associated with even recently washed cuttings, particularly when applied in combination with physical drying of the cuttings. This level of force can thus provide a standard or benchmark to use for adjustment of vacuum conditions where more water is present, where a larger container is used, where temperature is higher or lower, etc. Thus, methods comprising applying a vacuum of about such strength or greater to remove extraneous water from a material is one embodiment of the invention.

From various aspects of this disclosure it will be clear that the removal of extraneous water does not have to be limited to application of heat or vacuum. In some aspects, however, heating can be advantageous, and, accordingly, application of high heat to remove extraneous water is one aspect of the invention. Thus, for example, the method comprises applying a temperature of more than about 100 degrees C. to material (e.g., about 100 degrees C.-about 130 degrees C., such as about 100 degrees C.-about 125 degrees C., about 100 degrees C.-about 115 degrees C., about 100 degrees C.-about 112.5 degrees C., about 100 degrees C.-about 110 degrees C., or about 100-about 105 degrees C., or any of such ranges in which 100 is replaced with about 100.5 degrees C., about 101 degrees C., about 101.5 degrees C., or about 102 degrees C.) for a suitable period of time, typically at least about 20 seconds, at least about 30 seconds, at least about 40 seconds, at least about 1 minute, at least about 75 seconds, at least about 90 seconds, at least about 100 seconds, or at least about 2 minutes, or longer, such as about 0.5-15 minutes, about 0.5-12 minutes, about 0.5-10 minutes, about 0.75-7.5 minutes, about 0.75-3 minutes, or about 0.8-4 minutes, is, in some embodiments, employed to remove extraneous water, either alone or in combination with other methods, such as application of vacuum or physical water-removal methods. According to embodiments the water removal step, whether performed by heat, vacuum, physical methods, or a combination thereof, is performed in less than about 10 minutes, less than about 6 minutes, less than about 5 minutes, such as about 4 minutes or less, about 3 minutes or less, about 2.5 minutes or less, about 2 minutes or less, about 1.5 minutes or less, or even about 1 minute or less. In some embodiments, the method comprises consideration of the applicable factors, such as amount of water present, average pore size of the material, pressure and/or temperature, and enclosure size, if any, as well as amount of material present, and the method comprises adjusting applicable water removal variables accordingly (e.g., temperature and/or pressures applied, time of application, or other conditions described herein), such as in automated methods of the invention in which a computerized system of analysis and/or control is employed to handle the operation of the method, particularly when many samples are to be used in the method.

The removal of extraneous water typically will not cause the extraction of 10% or more, such as 7% or more, or 5% or more of the release-resistant water in the material. Thus, for example, methods of the invention can be characterized in that the step of removal of extraneous water results in extraction of less than about 4%, less than about 3%, less than about 2%, less than about 1.5%, less than about 1%, less than about 0.5%, less than about 0.25%, less than about 0.1%, or less than about 0.05%, e.g., less than about 0.01% of the release-resistant water in the material. In some embodiments, no detectable amount of release-resistant water is extracted from the material in the performance of removing extraneous water.

The removal of extraneous water will sometimes be performed in an enclosure, container, or closed system, as discussed elsewhere herein (typically where the transmission of water is not permitted as the container, enclosure, or system is water impermeable). However, in other embodiments, the removal of extraneous water will be performed, in whole or in part, in open/exposed conditions. In some embodiments this provides an advantage in terms of the removal of such water from the material. In some embodiments, however, the material will thereafter be placed in an enclosure, container, or closed system, which is at least substantially impermeable to water gain/loss, prior to the application of at least some of the release-resistant water analysis or release-resistant water extraction step (if performed).

In one embodiment, the step of removing extraneous water comprises subjecting the material to a vacuum pressure that extracts a measurable amount of organic volatile compounds in the material, as described in the '031 application (which is sometimes described as "rock volatiles stratigraphy" or "rock volatiles analysis"), thereby allowing the organic volatile compound analysis methods of the '031 application and this frequently performed first step of the present invention to be simultaneously performed. These organic compounds are predominately, overwhelmingly, or substantially entirely composed of material-associated volatile compounds, rather than compounds contained in fluid inclusions, which are the subject of older, fluid inclusion analysis technology which I helped to pioneer decades ago. According to embodiments, at least about 70% of such organic volatile materials (e.g., at least about 80% of the organic volatile materials, at least about 90% of the organic volatile materials, at least about 95% of the organic volatile materials, at least about 98% of the organic volatile materials, or at least about 99% of the organic volatile materials) are not contained in fluid inclusions.

Where the method comprises extracting the release-resistant water, the extraction of release-resistant water can be accomplished by any method that results in a release of a measurable amount of release-resistant water. Such methods can include application of high heat (e.g., heat at temperatures above about 120 degrees C., such as above about 130 degrees C., such as above about 150 degrees C., such as above about 170 degrees C., such as above about 200 degrees C.) and/or application of strong vacuum (marked by very low pressure, e.g., vacuum that is at least about 125%, at least about 150%, at least about 200%, at least about 300%, or at least about 500% stronger, lower, or both, than any of the vacuum pressures described herein with respect to the removal of release resistant water). As discussed above, the minimum suitable conditions for extraction of release-resistant water will dependent upon a number of factors, and the method can comprise a step of analyzing such factors and adjusting the application of conditions to ensure that a measurable amount of release-resistant water is obtained in each performance of the method. Typically, so long as a significant amount of structural water is not released in the process, the extraction of release-resistant water can be performed using relatively aggressive methods as compared to the removal of extraneous water. According to embodiments, less than about 5%, such as less than about 2%, such as less than about 1%, e.g., less than about 0.5% or less than about 0.2% of the water analyzed as release-resistant water will comprise structural water released from water-associated minerals (e.g., water contained in crystalline mineral compounds), such as in gypsum. An example of a suitable vacuum force for removal of release resistant water from most petroleum cuttings is application of a vacuum force of about 2 millibars (e.g., about 1.5-2.5 millibars, about 1.25-2.75 millibars, about 1-3 millibars, or about 0.8-about 4 millibars) to a sample of 300-500 microliters of cuttings for a period of at least about 5 minutes (e.g., about 4-12 minutes, about 5-15 minutes, about 5-10 minutes, about 6-10 minutes, about 6-9 minutes, about 7-9 minutes, or about 7-8 minutes) in a suitable container, e.g., a cylindrical container, that is impermeable with respect to water and which has a diameter of about 0.25 inches and a length of about 3.5 inches (or similar area in a different shape), at about room temperature. As noted elsewhere, the extraction of release-resistant water will often be such that a small amount or no detectable amount of structural water is released in the process (and thus contained in the measured/captured release-resistant water) (e.g., less than about 3%, less than about 2%, less than about 1%, less than about 0.5%, less than about 0.1%, or less than about 0.01% of the measured release-resistant water will be composed of structural water from water-containing mineral compounds contained in the material).

An extracted release-resistant water aliquot can be measured by any suitable method of measuring water. In one aspect, the measurement is performed by capacitance manometry, e.g., via a capacitance manometer. In aspects, capacitance manometry is used to measure at least a portion of the extracted release-resistant water. In other embodiments, the measurement of the release-resistant water extraction is also or alternatively performed with a humidity meter, application of a chemical assay, calculation of changes in mass of the material, or a combination of any thereof. In one aspect, the release-resistant water in the material can also or alternatively be measured by mass spectrometry analysis. This can comprise analyzing the amount of water molecules, directly, but also or alternatively can comprise measuring other compounds (e.g., $H_2$), elements, or ions, which individually or in some combination(s) are indicative of the amount of water in the material. Focusing on water-associated ions or elements can, in aspects, improve the analysis over analyzing water molecules via mass spectrometry. According to certain aspects, mass spectrometry is not used to analyze release-resistant water. In aspects, mass spectrometry is unsuitable for the methods provided by the invention. In aspects, water associated with materials tested in the methods of the invention could detectably or significantly impair the reliability of the analysis provided by the method, such as, e.g., detectably or significantly impair the reliable operability of a mass spectrometer, detectably or significantly impact the quality of the results, or any combination thereof. In aspects, methods other than mass spectrometry provide detectably or significantly more reliable results, faster results, provide for more efficient (e.g., more portable, or economically feasible) testing, or any combination thereof. In aspects, capacitance manometry, humidity metrics, chemical assay, calculation of changes in mass of the material, or other similar such analytical techniques can be used in addition to, or in place of, mass spectrometry to measure release-resistant water in material(s).

According to embodiments, the material can be mechanically disrupted prior to the extraction of the release-resistant water, and in some cases such a disruption step is performed before even the entire process of removing extraneous water is complete. For example, a method can comprise a step of washing/rinsing samples, removing the wash/rinse water plus very easily removable other extraneous water through application of one or more physical drying methods, mechanically disrupting at least some, most, substantially all, or all of the samples, further applying a method to remove extraneous water from the disrupted samples (e.g., by application of heat and/or vacuum pressure), and then continuing on to either directly (in-situ) analyzing the release resistant water content left in the samples or extracting the release-resistant water (e.g., by applying a relatively very strong vacuum and/or relatively very high heat) and measuring at least a portion of the extracted release-resistant water. The step of mechanically disrupting the material can be done by directly disrupting the material, indirectly disrupting the material (e.g., where the material is in a container and the container is disrupted, e.g., by crushing, and thereby imparts some of the crushing force to the contained material), or a combination thereof, in one or more steps. Suitable disruption can be any amount of disruption that detectably or significantly enhances the extraction/measurement of release resistant water in material (in a particular material, always, on average, or in a significant number of cases). For example, in one embodiment, material is subjected to a physical disruption before removal of extraneous water, such as in the formation of cuttings by use of a specialized drill, as discussed elsewhere herein, some extraneous water is removed by application of physical drying, the dried samples are then further physically disrupted, directly or indirectly, such as by crushing, subjected to further extraneous water removal methods (e.g., application of vacuum pressure and/or heat), and the extraneous-water free samples are either directly evaluated for release-resistant water content or some of the release-resistant water is extracted and at least some of the extraction measured, optionally in an enclosure. In some embodiments, some or all of these steps are performed in a container that is at least substantially water impermeable (except for being selectively water vapor permeable, such as through the insertion of a needle). In some embodiments such a container is a disrupt-able/disruptable water impervious container (a container that can be subject to physical disruption of materials contained therein while still retaining such water impermeability characteristics, as exemplified further herein and in the disclosure of the '031 application).

Methods of the invention often are performed on collections of materials, such as collections of samples obtained from different parts of a geologic unit, such as different portions of a site, e.g., different portions of a petroleum well or petroleum well exploration area, such as a play. In aspects, methods of the invention are performed on collections of samples obtained from different parts of a petroleum well. Thus, for example, methods such as those described both above and below herein can comprise repeating most or all of the steps of the method numerous times upon at least about 10 samples (e.g., at least about 20 samples, at least about 30 samples, at least about 50 samples, at least about 70 samples, at least about 100 samples, or more, such as about 20-200 samples, about 10-1000 samples, or about 15-1500 samples, about 50-1500 samples, 75-1500 samples, or about 100-1500 samples). According to embodiments, each such sample or some number of samples analyzed in such a method are separated by each other in at least one dimension (vertical distance and/or horizontal distance) by at least about 30 feet, at least about 50 feet, at least about 60 feet, at least about 75 feet, at least about 100 feet, at least about 150 feet, at least about 200 feet, at least about 250 feet, at least about 300 feet, or by a distance of about 20-200 feet, about 30-300 feet, about 30-240 feet, about 25-275 feet, about 25-250 feet, about 30-180 feet, about 30-150 feet, about 25-100 feet, or about 30-90 feet), wherein the amount of release-resistant water in the material is indicative of the location of petroleum deposits in different areas of the petroleum well. According to embodiments, the area is a petroleum exploration or production site that is associated with a low visibility play, such as a fresh-water play/area (e.g., a site located in or otherwise associated with a significant amount of fresh water or that otherwise is recognized as a freshwater play/site/area given teachings in the art). According to other embodiments the method is performed on a collection of petroleum cuttings from a horizontal well (as recognized in the art, it being noted that horizontal wells and areas thereof can vary significantly in depth, but are still considered horizontal wells so long as, e.g., such wells maintain some, significantly, or mostly horizontal directionality in most, substantially all, or all of the relevant area/site). In such a well, at least about 75%, such as at least about 85% of the area of the horizontal petroleum well from which the samples were obtained will typically be contained with a vertical zone of about 50 feet or less, such as about 20 feet or less, about 15 feet or less, or about 10 feet or less. In other embodiments, the method is performed also or alternatively on vertical production or exploration wells.

In petroleum production settings the steps of removal of extraneous water, measurement of release-resistant water (and extraction of a portion of the release-resistant water if applicable), and analysis thereof are typically performed relatively quickly, such as within less than about 15 minutes, less than about 10 minutes, or less than about 8 minutes, e.g., less than about 7 minutes, less than about 6.5 minutes, less than about 6 minutes, less than about 5.5 minutes, less than about 5 minutes, less than about 4.5 minutes, less than about 4 minutes, less than about 3.5 minutes, less than about 3 minutes, or less than about 2.5 minutes (e.g., about 2 minutes).

According to embodiments, such rapid methods are employed to provide a "real time" analysis of drilling operations, which can be used to actively direct future drilling direction and/or characteristics, or direct other operations, such as determining where to frack. In real time steering of petroleum drilling the method is typically performed on samples, such as drill cuttings, close to when such cuttings reach the surface. According to embodiments, the method is initiated on cuttings within an average time of about 20 minutes or less of such samples reaching the surface, such as less than about 15 minutes of reaching the surface (i.e., such cuttings are less than about "15 minutes old", such as less than about 12 minutes, such as less than about 10 minutes, such less than about 7 minutes, such as less than about 5 minutes, such as less than about 3 minutes, or such as about 2 minutes of such samples reaching the surface, e.g., within about 90 seconds, within about 75 seconds, within about 60 seconds, or within about 45 seconds of such samples reaching the surface. Thus, the time period between the samples reaching the surface to the completion of analysis in such embodiments cancan be, e.g., about 2-20 minutes, such as about 2-15 minutes, about 2-12 minutes, about 2-10 minutes, about 2-9 minutes, about 2-8 minutes, or about 2-7 minutes, 2-6 minutes, or 2-5 minutes, such as about 1.5-9 minutes, about 1.5-7.5 minutes, or about 1.5-6 minutes, or about 3-12 minutes, about 3-9 minutes, about 3-7.5 minutes, or about 3-6 minutes.

The speed of analysis can be increased by avoiding the step of extraction of the release-resistant water. Moreover, directly analyzing release-resistant water in a material can expand the applicability of the invention. As such, in an alternative exemplary embodiment the invention provides a method for analyzing a material containing release-resistant water comprising: (a) removing at least about 99% of any water associated with the material that is removable from the material by subjecting the material to a temperature of at least about 100 degrees C. water at normal atmospheric pressure ("extraneous water") from the material to obtain extraneous water-free material; (b) measuring an amount of remaining water remaining in the material ("release-resistant water") without extracting the release-resistant water, and (c) using the measurement of the amount of release-resistant water to assess the characteristics of the material. The analysis of release-resistant water in-situ in a material can be performed by any suitable method. Suitability will vary with the nature of the material and the location of analysis, among other factors that will be understood by those of ordinary skill in the application of such analytical techniques. Thus, according to exemplary embodiments, the detection of release-resistant water in-situ will comprise measuring water in the material through one or more of thermal gravimetric analyses, differential scanning calorimetry, spectroscopic methods such as NMR, MM, Raman spectroscopy, and Infrared Spectroscopy, and methods comprising weighing the material prior to and after removal of the extraneous water. Where such a method is directly applied to portions of a geological unit, the method can be used to generate a map of the unit, such as, e.g., a map of a geological area, region, or geological feature, without the removal of the material.

According to another particular exemplary embodiment, methods of the invention can comprise steps equivalent or substantially similar to the following: (a) placing a material in an enclosure such that the material is isolated from the environment; (b) removing substantially all of the extraneous water associated with the material from the material, (c) removing substantially all of the released extraneous water from the enclosure; (d) applying an extracting force to the sample of material in the enclosure, wherein the extracting force is capable of causing the release of a detectable amount release-resistant water from the material if present, and (e) measuring the amount of release-resistant water released from the performance of step (d).

As noted above, methods of the invention, including the particular method described in the preceding paragraph, can be performed with any suitable type of material. The material typically will be a material that is expected to possibly contain release-resistant water. For example, the material can be, in aspects, a material that is known to contain small pores and to be associated with water deposits or having a likelihood of being associated with water deposits and having a likelihood of being associated with petroleum deposits, e.g., due to proximity to known deposits of one or both.

As noted above, although the term "release-resistant water" (and similar terms) is/are used throughout this description, the method can apply to any suitable fluid that can be contained in material and is especially applicable to aqueous fluids containing additional substances in addition to water.

The materials are typically at least primarily solid, substantially consist of solids, or are substantially all solids, but will often be associated with some amount of extraneous water (which also can be in the form of an aqueous fluid rather than pure water) and/or some amount of release-resistant water. The material will often be material from a geologic site, but other materials could be the subject of analysis, such as those described in the '031 application. A commonly used material in the context of the invention is a petroleum drill cutting, which are also described in detail in the '031 application and the references incorporated therein.

Figure 4:
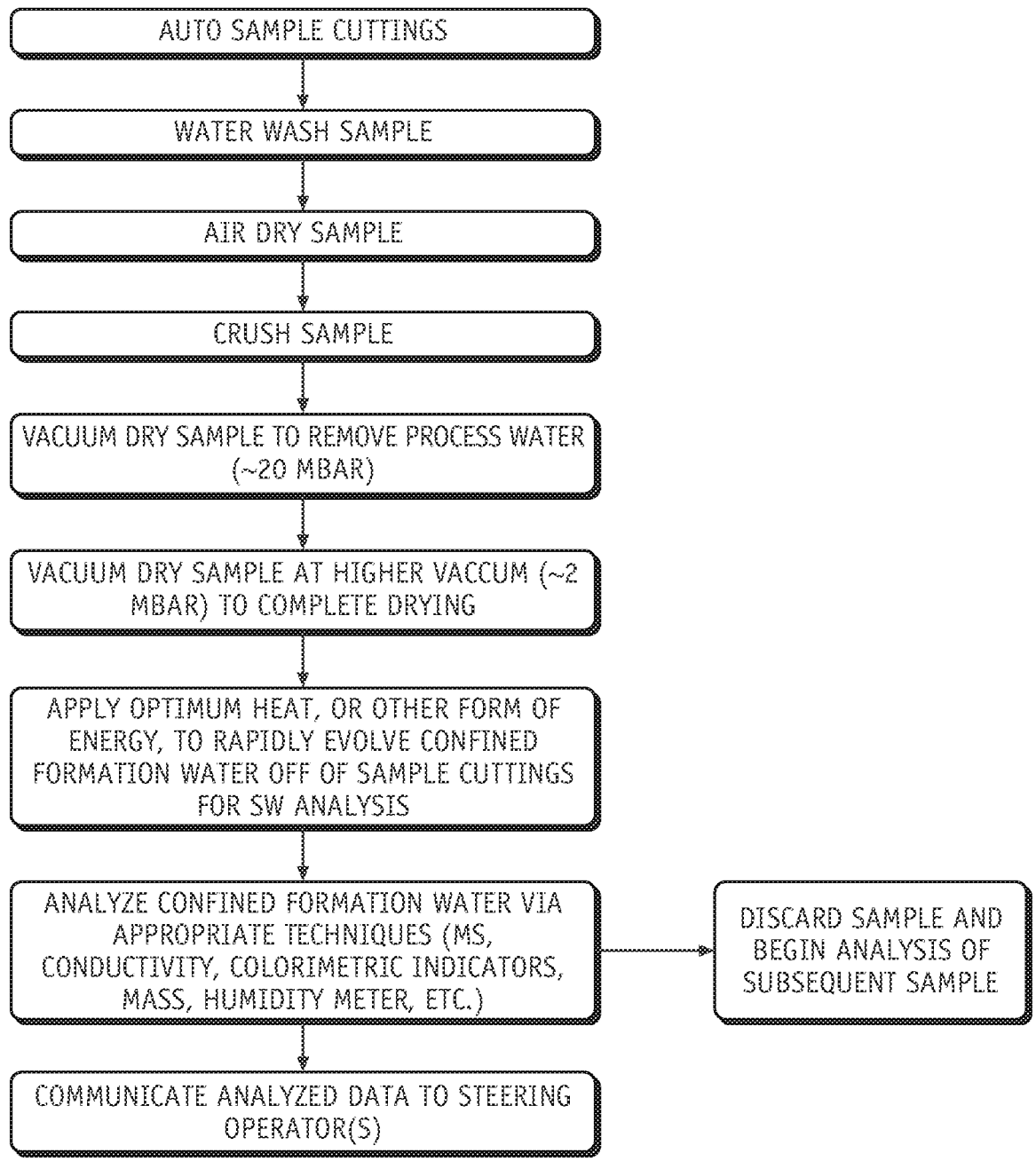
FIG. 4 is a flow chart providing an overview of steps of an exemplary inventive method.

An overview of one illustrative method of the invention, as applied to petroleum drill cuttings, is provided in FIG. 4.

In that exemplary method, cuttings are obtained through automatic sampling of cuttings generated at a drill site. Typically, and advantageously, the cuttings are collected in or directly from the flow line, prior to any exposure to a shaker table or corresponding device, which might cause excessive release of release-resistant water from the cuttings prior to analysis. The cuttings can, in aspects, be auto-sampled, as indicated, collected by an automatic (periodic or random) collection strategy.

The cuttings collected for analysis (each a "sample") in the method illustrated in FIG. 4 can then optionally be washed to remove debris, chemicals, etc., from the cuttings. This washing and other processes used in the drilling process, as well as the drilling process itself, typically causes the sample to be in association with extraneous water.

In accordance with the steps of the method described above, substantially all of the extraneous water (or "EW") is typically removed from each sample prior to any attempted extraction of release-resistant water (or "RRW"). In the exemplary method shown in FIG. 4, a two-step method is employed to remove extraneous water from the sample cuttings. First, the cuttings are subjected to air drying (a form of a physical water removal method). This step can be performed inside or outside of a device/container for performing the analysis (an "enclosure"). The samples are then subjected to vacuum drying to remove substantially all of the remaining extraneous water (in FIG. 4 labeled as "process water"). This step can be performed within an enclosure, such as an enclosed device (a container), which will be used for the remaining steps of the method, such as the device exemplified below and depicted in FIG. 5.

Removal of the extraneous water can be performed, as shown, by application of a drying vacuum, such as, in connection with a cylindrical container of about 0.25-inch diameter and about 3.25-inch length, at room temperature, a vacuum set at about 20 millibars, and operated for a period of less than about 9 minutes, such about 6 to about 9 minutes (e.g., about 6-about 7 minutes). It can be the case that this second extraneous water removal step is advantageously for a shorter period, such as less than about 3 minutes, less than about 2 minutes, or less than about 1 minute, e.g., by application of a stronger vacuum and/or application of heat, or by more thorough removal of water prior to application of the vacuum through physical water removal methods (such that there is less extraneous water to remove by application of the vacuum). The vacuum can, in aspects, also or alternatively be applied for a time period of longer than about 9 minutes when necessary to ensure removal of the extraneous water or otherwise considered desirable (e.g., vacuum can be applied for about 10 minutes, about 15 minutes, about 20 minutes, about 30 minutes, about 40 minutes, about 60 minutes, about 90 minutes or longer (e.g., about 5-90 minutes, about 10-75 minutes, about 15-60 minutes or about 5-60 minutes, about 5-45 minutes, about 5-30 minutes, about 1-30 minutes, or about 1-20 minutes).

Typically, the vacuum drying and/or extraction step of the method is performed at about room temperature (e.g., about 18-about 28 degrees C., more typically about 20-about 25 degrees C.), but the vacuum step will nonetheless cause the evaporation of substantially all the remaining extraneous water associated with the sample. The water vapor taken up by application of this vacuum step is then typically removed from the enclosure/association with the sample. In other embodiments, as noted elsewhere herein, the removal of extraneous water can comprise application of high heat, such as a heat of at least about 100 degrees C. (e.g., about 100-about 125 degrees C. or about 100-115 degrees C.), alone or in combination with the application of vacuum pressure.

To achieve faster drying and/or extraction through application of vacuum pressure the method can comprise applying increased pumping while vacuuming. In the methods exemplified in the Examples, the system of the '031 was used for both drying and for extraction of release-resistant water. That system comprises a small diameter needle configured to extract gas containing organic/hydrocarbon volatiles from cuttings and similar materials contained in sample containers. Accordingly, the pumping through such portions of the system is limited.

I envision that devices, such as those according to the embodiment of the invention illustrated in FIG. 6, can have a diameter in the corresponding area that is at least 20×, at least 20×, at least about 25×, at least about 50×, at least about 75×, or at least about 100× the diameter of the device of the '031 application (in the needle of the device/system). I also envision the use of strong/fast dynamic pumps in devices of this invention, such as the device exemplified in FIG. 6, being employed in combination with application of vacuum pressure, such as exemplified elsewhere herein. The combination of such features will allow for extraction of detectable levels of release-resistant water in less than about 5 minutes, less than about 3.5 minutes, less than about 2 minutes, less than about 1.5 minutes, or even less than about 1 minute. Such relatively fast times for drying and/or extraction of release-resistant water will be important in applications of the invention on petroleum well sites, especially where the method is used to direct drilling operations (i.e., to "steer" drilling).

The sample can be crushed by application of a mechanical force. The timing of the crushing step is the distinguishing characteristic between the exemplary method exemplified in FIG. 4 and the exemplary method exemplified in FIG. 5. In the method of FIG. 4, the crushing step is performed after the initial vacuum step for removing extraneous water. In the method shown in FIG. 5, the crushing step is performed after air drying the samples, but before the application of the extraneous water-removing vacuum (at about 20 millibars). Although not shown, it could be possible to also perform a crushing step during the application of vacuum or other process designed to remove extraneous water. The crushing step can, in aspects, be performed by applying a crushing force directly on the samples or by applying a crushing force on a container containing the samples (such containers and crushing steps are exemplified in the '031 application).

The crushed and dried sample cuttings are then subjected to resistant-water removal step, which can comprise, and typically consists of, application of a vacuum pressure of about 2 millibars (as illustrated here). This step, alone, or in combination with application of other forces, such as application of energy, heat, etc., shown as the next step in the flow chart, causes the extraction of release-resistant water (labeled as "confined formation water") from the cutting sample and the evaporation/evolution of such release-resistant water (thereby forming water vapor).

In an alternative set of embodiments, after completion of the step of the method where extraneous water is removed, the remaining release-resistant water can be analyzed in-situ by using methods such as capacitance manometry, thermal gravimetric analyses, differential scanning calorimetry, nuclear magnetic resonance ("NMR"), magnetic resistance imaging ("MRI"), or other spectroscopic technique such as Raman spectroscopy or infrared spectroscopy or similar method that would not require the extraction of the release-resistance water from the sample. Typically, application of such methods is coupled with removal of substantially all the extraneous water associated with the sample, and the sample commonly remains in a dehydrated state until analyzed. In yet another embodiment, the sample of cuttings can be weighed after the extraneous water removal step, and again after removal of release-resistant water is sufficient if no other mass, such as oil or gas, is lost from the sample during removal of the release-resistant water. The difference in masses would, in the performance of such a step, be representative of the lost release-resistant water. In many of these analytical methods, the sample is enclosed, such as by being in a container, which is water impermeable except for selective intrusion of the container, such as by opening of the container to a passageway or entry of the container via an inserted needle, as discussed in the preceding paragraphs and also exemplified in the '031 application.

The water vapor formed from the evaporated portion of the confined formation water (release-resistant water) is subjected to one or more analytical methods, which include mass spectrometry ("MS") analysis, conductivity analysis, colorimetric indication analysis, and/or direct or indirect measurements of mass, humidity, etc., as discussed further elsewhere herein.

Figure 5:
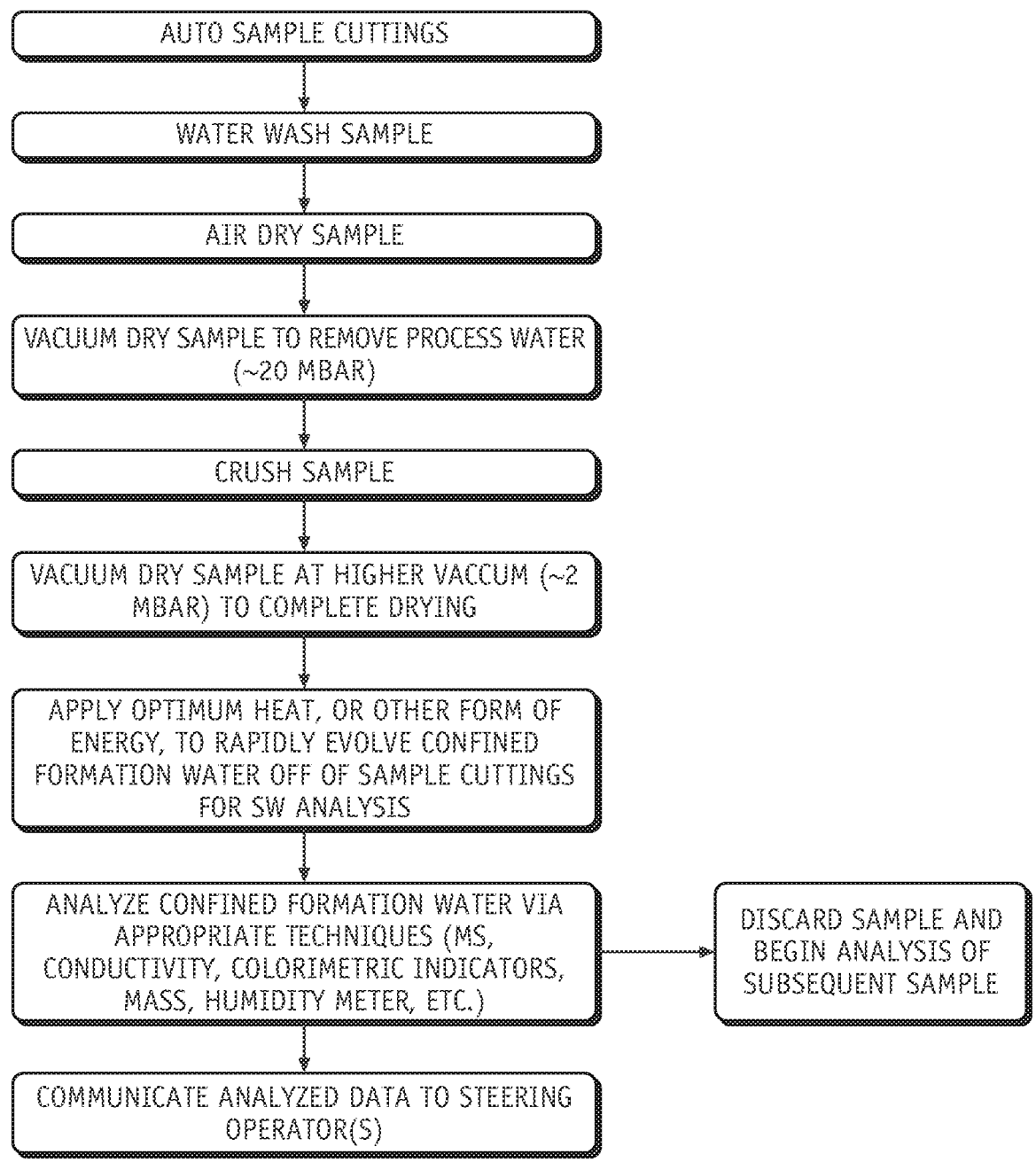
FIG. 5 is a second flow chart providing an overview of steps of a second exemplary method of the invention.

An analyzed material or sample can then be discarded, the data captured/relayed, and, in a typical embodiment, the cycle repeated with the next sample in the series. The method is performed on typically dozens, scores, and more often hundreds of samples, and the results can be used to generate one or more "maps" of an associated geologic unit of material, such as a geologic region or area or, e.g., specific site, based on the results of the analysis applied to the samples (e.g., relative Sw data, based on the relative amount of release-resistant water detected in the samples). In the embodiments of FIGS. 4 and 5, the data is relayed to a well operator who then uses the data in real time or near real time to direct the drilling operation based on the results of the analysis, thereby improving the amount of oil production from the well based on the evolving understanding of the geologic unit provided by the results of the method.

Having provided this overview of particular exemplary embodiments, a description of the general steps and components of the invention will be provided, to assist those applying the disclosure in understanding the full scope of the invention.

As noted above, the method of the invention will typically include a step of removing extraneous water from the material to be analyzed. Usually this will mean removing substantially all of the extraneous water from the material.

The removal of extraneous water can be carried out using any suitable method. Typically, the method should not include steps that will risk loss of so much of the release-resistant water that the analysis of the material becomes compromised. As such, methods of freezing the material, especially if such methods comprise subjecting the material to temperatures below about -20 degrees C. or below about -30 degrees C. will typically be avoided to avoid inducing significant additional cracking in the material at this stage in the process (when extraneous water can be present). Typically, also, methods of heating the material, especially for long period of time, e.g., about 15 minutes or more, about 20 minutes or more, or about 30 minutes or more, in an oven or other condition where the temperature is at least about 85 degrees C., at least about 90 degrees C., at least about 95 degrees C., or about 100 degrees C. or greater, also are avoided, as such temperatures at the extraneous water removal (i.e., "drying") step can, in aspects, cause the loss of too much release-resistant water. This is not to indicate that heat cannot be used or is not often important in the drying step. It can be that some amount of heat can be applied, such as lower heat levels, and heat can be combined with application of other tools for drying the material. In fact, in some cases significant heat (e.g., a temperature of about 50-about 90 degrees C., such as about 55-about 85 degrees C., or about 60 degrees to about 80 degrees C.) is applied for a period of one minute, two minutes, three minutes, at least about 5 minutes, or longer, to assist in drying or in the extraction of release-resistant water. Alternative and additional suitable methods are described in other portions of this disclosure.

Chemical water removal techniques, such as exposure to desiccants, also or alternatively can be suitable for drying the material. In some cases, as noted above, air drying also or alternatively can be an advantageous first step in the drying process.

Application of vacuum pressure or a similar force in an enclosure, such as a suitable container, is a workable way of removing extraneous water from a material. For example, application of a vacuum pressure of about 20 millibars, for a period of about 6 to about 9 minutes (e.g., about 7-8 minutes), at a suitable temperature (e.g., close to room temperature, such as about 18-28 degrees C., more typically about 20-25 degrees C.) can cause extraneous water to evaporate, and the generated water vapor can then be readily removed by the vacuum from contact with the material (with respect to containers having sizes discussed elsewhere herein and the performance of the method at room temperature). The application of similar vacuum force under different conditions can also be performed, as discussed elsewhere herein.

According to embodiments, the steps of drying extraneous water, extracting release-resistant water, and the conditions of analyzing the release-resistant water are selected and/or controlled so that minerals in the material(s) having water in their crystalline structure, such as clays and gypsum, do not decompose in any significant part (e.g., no more than about 5%, more than about 2%, more than about 1%, or more than about 0.1% of these materials undergo decomposition of water). The decomposition of such crystalline materials can lead to the release the structural water associated with the material(s). Such a release of water could, in circumstances, overcome any extraction of release-resistant water or result in inaccurate measurement of the amount of release-resistant water extracted from the material. As such, methods that cause the release of such structural water can be avoided as a characteristic of the method, at least according to some embodiments.

Either before, during, or after drying, the material is typically subjected to a mechanical disruption step. "During drying" can mean between steps of a drying process, as exemplified by the method shown in FIG. 5 and/or can mean while a drying process is underway (e.g., where the material is crushed while also under a drying vacuum pressure/condition). Mechanical disruption can be performed by any step in which the material is broken to form more pieces/particles and/or to exposed surface area of the material. Thus, mechanical disruption will typically include processes such as crushing, grinding, cutting, and the like. According to embodiments, mechanical disruption does not comprise application of high heat (temperatures of at least about 80 degrees C., at least about 90 degrees C., at least about 95 degrees C., or at least about 100 degrees C.); freezing; and/or chemical deterioration of the material. Crushing is an effective way to perform mechanical disruption. Crushing can be accomplished by directly crushing the material or can be applied to a container containing the material (indirect crushing). Methods of indirect crushing of materials, such as petroleum drill cutting samples, are provided in the '031 application.

According to embodiments, the material is not subjected to mechanical disruption outside of the enclosure or an environment that would maintain a detectable amount of release-resistant water in the material before the step of removing extraneous water from the material or the step of extracting release-resistant water from the material. Thus, for example, in a specific embodiment where the method is performed with a collection of cuttings at a petroleum drill site, the method comprises the collection of cuttings from the flow line or in some other manner where the cuttings are collected prior to being in contact with a shaker table, which commonly is used in processing cuttings. Other types of cutting, vibration, crushing, and other disruptive processes outside the context of either an enclosure for the performance of the method and/or an environment that acts as an enclosure (e.g., the subterranean context of an oil well) can be avoided to reduce risk of loss of any previously present release-resistant water.

As already indicated, after the material is crushed and dried it will be subjected to an extraction step to cause the release of an analyzable amount of release-resistant water. The extraction of release-resistant water can be performed under any suitable method. A number of factors, however, can be relevant to the optimal extraction of release-resistant water. First, the extraction should not decompose crystalline mineral materials resulting in the release of structural water from such materials in significant amount leading to an inaccurate measurement of release-resistant water. Second, and more generally, the extraction step should preserve a detectable amount of release-resistant water and do so in a manner where a relatively accurate measurement can be obtained. Finally, the force applied to the material to extract the release-resistant water has to be able to cause the release of a measurable amount of release-resistant water.

Vacuum force is a method that can be used for the extraction of release-resistant water; for example, application of a vacuum of about 2 millibars under suitable conditions of time, temperature, etc., especially with respect to applying the method to about 300-400 microliters of a rock sample in a cylindrical container of about 0.25-inch diameter and about 3.25 inches of length, when performed at room temperature. As discussed above, using the system of the '031 application, extraction times of about 6 to about 9 minutes (e.g., about 7 to about 8 minutes) is one possible approach. However, using the principles discussed elsewhere herein, e.g., by using a relatively large diameter enclosure and one or more pumps, the speed of extraction can be sped up to less than about 5 minutes, less than about 4 minutes, less than about 2.5 minutes, less than about 2.25 minutes, less than about 1.75 minutes, or less than about 1.25 minutes (e.g., about 1-4.5 minutes, about 1-3.25 minutes, about 1-2.33 minutes, or about 0.75-1.75 minutes). Other forces that are similar in strength also can, in aspects, be possibly used to extract release-resistant water from the material. The type of force or other means selected for extraction of the release-resistant water will vary with the means for analysis, the material, and other factors that will be determinable with application of reasonable experimentation given the disclosure provided here. For example, some analytical methods will require very little release-resistant water, whereas other methods (e.g., simple humidity detection methods) can require relatively more release-resistant water in order to provide a useful absolute or relative measurement.

In some embodiments it is necessary or advantageous that a substantial portion, and typically a majority, if not more (e.g., at least about 75%, at least about 90%, or at least about 95%) of the release-resistant water is converted to water vapor in the performance of the extraction step, as is the case with application of vacuum pressure under the above-described conditions. In such embodiments, the method typically comprises directly or indirectly measuring the amount of release-resistant water present as water vapor. Indirect methods of measurement will typically measure components of water, rather than water itself. For example, in the use of certain mass spectrometers it can be advantageous to measure hydrogen ($H_2$) formed from the breakdown of release-resistant water vapor in the mass spectrometer rather than measuring the amount of water directly.

The application of vacuum pressure both for drying (e.g., at about 20 millibars) and/or for extraction of release-resistant water (e.g., at about 2 millibars) are, according to embodiments, performed at about room temperature (e.g., about 18-about 28 degrees Centigrade (C), more typically about 20-about 25 degrees C.). Alternatively, such methods can be performed at a temperature of between about 20 or about 25 degrees C. and about 75, about 80, about 85, about 90, or about 95 degrees C. In other methods, as mentioned elsewhere herein, the extraction of release-resistant water is performed at temperatures of about 100 degrees C. or higher, and often at temperatures in excess of temperatures that would be suitable for removal of extraneous water, e.g., temperatures of about 125 degrees C. or higher, such as about 135 degrees C. or higher, or about 150 degrees C. or higher, such as about 170 degrees C. or higher.

The analytical step of the inventive methods described herein can be carried out by any suitable device or combination of devices. As exemplified herein, mass spectrometry analysis is one method that can be used to analyze release-resistant water and thus determine properties of materials, despite the long-held view that such data would not provide meaningful information. Mass spectrometric analysis has also been used to perform many of the methods described in the '031 application, demonstrating that such systems can serve a dual function.

Also or alternatively, humidity meters, which are well known in the art, can be used to assess the amount of release-resistant water present after extraction from the tested material.

Also or alternatively, one or more chemical assays can be used to assess the amount of release-resistant water present after extraction. For example, according to embodiments the release-resistant water is contact with an absorbent that takes in substantially all of the release-resistant water and the method comprises measuring a mass change in the absorbent material. In another aspect, a color change chemical is used to assess the release-resistant water content. One example of such a chemical assaying material is calcium sulfate materials, such as Drierite-type desiccants, which have the ability to change color readily based on the amount of water present and which also are considered "rechargeable." The characteristic of the chemical assay being rechargeable is important in the context of systems, devices, and methods in which it is envisioned that tens, scores, hundreds, or even thousands of samples of material, such as from different parts of a geologic unit, are subjected to release-resistant water analysis.

In some embodiments it can be advantageous to concentrate the release-resistant water. For example, in an embodiment the release-resistant water is extracted in the form of water vapor and the method comprises a step of concentrating the water vapor, so as to make analysis easier, more accurate, or more feasible. A variety of concentrating ("trapping") methods are known in the art and can be employed in such analysis. In one embodiment, a cryogenic trap, such as the type exemplified in the '031 application, is used to concentrate the water vapor formed by a vacuum extraction method and released vapors from the cryogenic trap are then subjected to mass spectrometry analysis.

The methods of the invention do not require, and in some embodiments do not include, steps commonly employed in material analysis, such as those steps that have been required to be part of the analysis of geologic samples in the prior art. According to embodiments, the method does not comprise a step of oven-heating the material. In more specific embodiments the method lacks any step in which the material is heated to a temperature of about 75 degrees C. or more, about 80 degrees C. or more, about 85 degrees C. or more, about 95 degrees C. or more, or about 100 degrees C. or more, for any period, a period of more than about 1 minute, a period of more than about 2 minutes, a period of more than about 5 minutes, a period of more than about 20 minutes, a period of more than about 30 minutes, a period of more than 40 minutes, or a period of about 60 minutes or longer. The methods of the invention also or alternatively can be characterized in that the method lacks any step of freezing the material, especially at very low temperatures (e.g., the method does not include any step of subjecting the material to a temperature of less than about –20 degrees C., less than about –30 degrees C., or less than about –50 degrees C.).

However, in another aspect, freezing and thawing after the extraneous water is released but prior to the extraction, concentrating, and analyses steps is performed, as the inclusion of such a step can, in aspects be advantageous in that it can open any present microfractures or similar structures in the material further and allow the release-resistant water they hold to escape more easily. The chilling temperature typically would be monitored and set to avoid reaching the level of breaking any present and intact fluid inclusions. In another aspect of the inventive methods, drill bits designed to induce micro fractures before the cuttings are formed in the drilling process also or alternative employed, to optimize the process by creating the optimal number of micro fractures in the cuttings or other geologic material to be analyzed. Other methods that accomplish similar results also or alternatively can be applied. Thus, the methods of the invention can include a step of increasing and/or optimizing any present release-resistant water-associated structures in the cuttings or other materials. This step can be performed through an optional drilling step, using special drill bits, etc.

Drill bits that have appendages, or special designs, or are otherwise configured to optimize the number of micro fractures that are useful in the performance of steps such as those described above are another feature of the invention and a component of systems of the invention. The application of such methods can, for example, increase the amount of such fractures, the volume of such fractures, the average diameter of such fractures, or a combination of any or all thereof, by, e.g., at least about 5%, at least about 10%, at least about 15%, at least about 20%, or at least about 25%.

In still another aspect, the invention does not include any step including gas chromatography analysis. In yet another aspect, the inventive method does not include any step of analyzing fluid inclusion contents and/or hydrocarbon or organic acid content of volatiles released from materials (e.g., petroleum cuttings) or contained within the release-resistant water (e.g., the method does not comprise any measurement of oil saturated water or any of the compounds highlighted in the '031 application, such as formic acid, acetic acid, and the like).

As indicated above, particularly advantageous applications of the method of the invention include the repeated performance of the steps described above on a number of samples. In some embodiments at least 10, at least 20, at least 50, at least about 100, at least about 150, at least about 250, at least about 300, at least about 400, at least about 500, at least about 750, at least about 1,000, or more samples of a material (such as about 100-10000 samples, about 150-5000 samples, about 200-2000 samples, or about 250-1500 samples) are analyzed, typically where most, substantially all, or all of the samples are different in characteristics, such as geologic samples obtained from different parts of a geological unit, e.g., geological site (e.g., an oil well). In such embodiments, the amount of release-resistant water obtained from the numerous samples analyzed by the method, even if only on a relative (comparative) basis, can be used to generate a plot or "map" of the geologic unit under study (e.g., petroleum well(s)). Thus, for example, where the samples are a collection of petroleum cuttings, as exemplified in the Examples provided herein, the plots of the amounts of release-resistant water obtained from samples can be used to map the location of petroleum deposits. Thus, e.g., the results of the method can be used as an index of water saturation ("Sw") and therefore can be used to locate oil and gas pay zones.

The inventive method is particularly useful in the context of horizontal petroleum wells, wherein, typically, over a substantial length of the horizontal well (e.g., at least about 75% of the well, at least about 80% of the well, at least about 85% of the well, or at least about 90% of the well) the well travels within (remains within) a vertical area of less than about 50 feet, less than about 30 feet, less than about 20 feet, less than about 15 feet, less than about 12 feet, less than about 10 feet, or less than about 7 feet (e.g., about 5 feet or about 5-10 or 5-20 feet). Given the limited vertical zone the samples are obtained from they will typically have similar geological characteristics, making the analysis of release-resistant water typically more effective.

As noted above, the methods of the invention can be combined with other known methods for the analysis of materials, such as for the analysis of petroleum-related materials including drill cuttings. Such methods include analytical methods that characterize the geological properties of the geological unit under study (such as ductility, hardness, permeability, and/or porosity), the amount and/or location of oil present in the geological unit, or both (e.g., conventional well logging, fluid inclusion analysis, core analysis, etc.). A number of such methods are described in the '031 application and the various references cited therein (e.g., conventional petroleum well logging methods, fluid inclusion analysis, gamma ray analysis, etc., and other such methods are known in the art, including petroleum fluid fingerprinting analyses, and the like). Such other methods can be considered "means for" material analysis or site analysis and, in aspects, can be considered a "step for" characterizing a material or site through analysis of several material samples or an area of material.

An advantageous aspect of the invention is the application of the method to geologic materials, such as petroleum cuttings, core samples, or the like, which are obtained from a geological unit, e.g., a geological site, that can be characterized as a "low visibility site" in the art, i.e., a site in which conventional well logging has substantially, measurably, or significantly reduced effectiveness or is considered ineffective. An example of such a situation is freshwater petroleum exploration and production sites, where conventional well logs are well known to be ineffective.

I envision embodiments of this invention wherein the method is applied at the site of petroleum exploration and production (e.g., within close proximity to the well site, such as within about 0.5 miles, within about 0.25 miles, or within about 0.1 miles of the site where well materials are brought to the surface). According to embodiments, petroleum cuttings are taken directly from a flow line, for example, using a device such as that illustrated in FIG. 6. According to embodiments, the data from performing the method is used to direct drilling in real time. In such contexts, rapid analysis of samples will be advantageous. Using principles described herein such as large volume containers and/or pumping in combination with application of effective vacuum, typically paired with simple analytical methods, such as chemical color assays or humidity detection, can lead to rapid drying, extraction of release-resistant water, and rapid analysis thereof. Such methods can, in aspects, be performed within about 10 minutes or less, within about 6 minutes or less, within about 5 minutes or less, within about 3 minutes or less, or even about 2 minutes or less (e.g., about 1.5-about 6 minutes, such as about 1.25-5 minutes or about 1.25 to about 3.75 minutes).

In the context of a petroleum site, the use of any equipment, materials, etc., that can lead to fire, sparks, etc., is a significant risk. As such, in some embodiments of the invention the number of steps carried out with such materials, devices, etc., is avoided. For example, vacuums and pumps used in performing the method can be powered by pneumatic sources, which are commonly present at drilling sites. Simple chemical humidity detectors or chemicals that can detect the relative amount of water present in an enclosure can be used to assess the relative amount of release-resistant water extracted by application of such vacuums and pumps. Color changes of color-sensitive desiccants can be remotely monitored using fiber optic lines to detect color changes using electronics a safe distance from the possum belly and similar remote monitoring methods (e.g., camera or other image capture methods and other remote color detection methods known in the art that might operate across distances) can be utilized to maintain safety.

Devices for Performing the Methods of the Invention

Although the devices of the '031 application can, in aspects, be used in the performance of the method of the invention, or steps thereof, as demonstrated by the Examples provided herein, in aspects other systems and devices can also or (i.e., and/or) alternatively, and in many cases more advantageously, be used to perform such methods. Such devices and systems make up an additional set of aspects of this invention.

In one exemplary embodiment, the invention provides a system for analyzing release-resistant water in materials comprising: (a) a collection component capable of capturing samples and delivering samples into an enclosed analytical device; (b) an optional washing component configured to wash delivered samples in an average time of about 1 minute or less; (c) a drying component capable of removing extraneous water from washed samples in an average time of about 2 minutes or less; and (d) an enclosed device comprising, (i) an optional sorting component for sorting samples from one another, (ii) an optional crushing component configured to crush the samples in an average time of about 1 minute or less, and (iii) an analytical component capable of analyzing the amount of release-resistant water in the dried material.

According to embodiments, the analytical component can comprise an in-situ water content analysis device or component that is capable of measuring release-resistant water still contained within samples after the removal of extraneous water. Such an in-situ water content analysis device or component can operate by a method that comprises one or more of capacitance manometry, thermal gravimetric analyses, differential scanning calorimetry, spectroscopic methods such as NMR, MRI, Raman spectroscopy, and infrared spectroscopy, and weighing the material prior to and after removal of the extraneous water, and thus components or devices with such capabilities can be incorporated into the system.

Also or alternatively, the system can include a release-resistant water extraction component capable of exerting an extraction force on the samples capable of extracting an analyzable amount of release-resistant water and wherein the analytical component analyzes release-resistant water extracted from samples. The extraction component of such systems can extract an analyzable amount of release-resistant water from samples that the system is configured to analyze, typically in an average time of about 5 minutes or less, about 4 minutes or less, about 3.5 minutes or less, about 3 minutes or less, about 2.5 minutes or less, about 2 minutes or less, about 1.75 minutes or less, or about 1.5 minutes or less.

In some embodiments the system will include a device, component, or sub-system for mechanically disrupting materials to be analyzed. In some cases it can be advantageous to separate the physical disruption of the material from the extraction of release-resistant water (where extraction is performed) or from the release-resistant water analytical component(s) of the system. Thus, in one exemplary embodiment the system comprises a first chamber containing the physical disruption component (e.g., a crushing component) and a separate second chamber comprising the extraction component and that comprises or is in communication with the analytical component, wherein samples are capable of flowing from the first chamber to the second chamber under automated or selectively controlled conditions. In other aspects, both processes are performed in the same chamber, vessel, etc.

The system can comprise analytical components (e.g., one or more sensors) that are applied upstream of the release water analysis, such as analytical components that analyze the sample, temperature, pressure, extraneous water content, etc., and that in some embodiments adjust one or more parameters of the method automatically or send signals to an operator concerning such parameters.

In some embodiments, such systems can include means for sorting liquid associated with the material, the material, or both. Thus, for example, such systems can include a material collection component that comprises channels for permitting the passage of a flow of liquid containing solid samples, e.g., a material collection component which can be coupled to a flow line or other part of a flow of material from a petroleum well or similar system. In some aspects such a system can include one or more tortuous path components, or both, to detectably or significantly control the flow of samples into and/or through the system.

The analytical component can include any of the various water analytical devices/components described herein, such as a capacitance manometer, a humidity meter, or an MM. In most embodiments the physical device for collecting such data will be coupled with a computer analytical system that can store the data, analyze the data, and often combine the data with other data, such as data from a corresponding wire log.

Such systems will typically include a communication component, for relaying data obtained from the analytical component to a well site operator (e.g., a data communication component such as an internet connection, Bluetooth connection, wireless radio communication component, hardwired communication (physically-connected communication) component, or known equivalents for similarly relaying data). The communication system is often coupled to the analytical system and/or can comprise its own data analytical components. The communication system can relay such information to other computer systems and/or directly to one or more operators or analysts. Analytical information can include, for example, comparison of the data for the analyzed sample or samples against historical data, averages, standards, and the like, such as information associated with samples obtained from a comparable location of a geologic unit, such as a geological area, region, or feature, e.g., a formation, analyzed similarly. As already noted, such information can be combined with, e.g., wire log data, fluid inclusion analysis data, or non-fluid inclusion organic compound volatiles data, and other data relevant to analysis of the material, e.g., gamma ray data, such as the types of data discussed in the '031 application.

In another exemplary embodiment, the invention provides a system for analyzing release-resistant water in materials comprising: (a) a collection component capable of capturing samples and delivering samples into an enclosed analytical device; (b) a washing component configured to wash delivered samples in an average of time of about 1 minute or less; (c) a drying component capable of removing extraneous water from washed samples in an average time of about 2 minutes or less; and (d) an enclosed device comprising, (i) a crushing component configured to crush the samples in an average time of about 1 minute or less, (ii) an extraction component capable of exerting a force on the samples which is capable of extracting release-resistant water from the samples in an average time of about 2 minutes or less, and (iii) an analytical component capable of analyzing the amount of release-resistant water in the enclosure.

The collection component of such systems can be any device or part that is configured to collect materials, such as samples from a geologic unit, such as petroleum drill cuttings from a petroleum well, from the environment, typically from a fluid flow containing samples, such as a flow of drilling mud comprising drilling cuttings for analysis. In some embodiments the collection component is selectively and/or automatically moveable, such that the component can be positioned in different locations for collection of samples, depositing the samples into a device for further processing and analysis, etc. In some embodiments the collection component is configured to allow the flow of material through the component while still providing for the collection of solid samples. Thus, in one aspect, the collection component is configured like a strainer, with slits, openings, etc., large enough to allow the flow of drilling mud or other carrier fluid, while being small enough to capture samples of interest.

According to embodiments, the enclosed device of the system can comprise two or more separated (or at least partially separated) chambers, which can comprise different components of the system and be used for carrying out different steps of the inventive method. Thus, for example, in one aspect the invention provides a system comprising a device that in turn comprises a first chamber containing the crushing component and a separate second chamber comprising the extraction component and that comprises or is in communication with the analytical component, wherein samples are capable of flowing from the first chamber to the second chamber under automated or selectively controlled conditions.

According to embodiments, the extraction component comprises a heating component, a vacuum component, or both. The heating component in some embodiments delivers heat with a maximum temperature of about 95 degrees C. or can be configured to provide temperatures in a range such as about 55-about 95 degrees C., about 65-about 95 degrees C., about 60-about 90 degrees C., or about 55 to about 85 degrees C. The vacuum component of the extraction component typically is capable of and in aspects can be configured to apply a vacuum pressure of about 2 millibars or any of the other vacuum pressures/ranges described elsewhere herein.

According to embodiments, the invention provides systems wherein at least one, at least two, or more valves are used to control the flow of the various components and forces of the system, particularly in an enclosed device or enclosed portions of a device/system. In one exemplary aspect, an enclosed device comprises a first valve for controlling the vacuum component and a second valve for controlling access to the analytical component.

The enclosed device of the system also or alternatively can comprise one or more gating components, one or more tortuous path components, or both, to detectably or significantly control the flow of samples through the enclosed device (e.g., detectably or significantly limiting the amount of samples in part(s) of the device/system, delaying the movement of samples in part(s) of the device/system, or both). Examples of such features are shown in the exemplary device of FIG. 6.

The system also typically comprises a sorting component to separate samples from one another. Exemplary sorting components can be conveyors, chutes, sorting wheels, and similar components.

The system also typically comprises a discarding component for removing analyzed samples from the system, usually by removing such analyzed samples from the enclosed device of the system.

According to embodiments, at least some of the components of the system, including a crushing component, are configured to be powered by a petroleum well pneumatic power system. Vacuum systems, valves, and other operational components can be similarly powered by such a system, thereby avoiding the use of potentially sparking components in the system.

Typically, a system of the invention will further comprise a communication component for relaying data obtained from the analytical component to a well site operator and one or more programmable controls for selectively operating or controlling, partially automatically operating or controlling, or automatically operating or controlling most or all operations of the system.

According to embodiments, the analytical component of the system comprises a device or component that is capable of measuring release-resistant water still contained within samples after the removal of extraneous water (e.g., an MM device, NMR device, or similar device). Accordingly, the invention also provides methods (modifications of the methods described above), wherein the step of extraction of release-resistant water is skipped and the method comprises such a step of in-situ measurement of release-resistant water (i.e., measurement of release-resistant water left in the sample or other material after removal of extraneous water). Such an analytical component can operate by performing methods that would not require the extraction of the release-resistant water from the sample comprising, for example, thermal gravimetric analyses, differential scanning calorimetry, spectroscopic methods such as NMR, MM, Raman spectroscopy, and infrared spectroscopy, as well as methods comprising weighing the material prior to and after removal of the extraneous water so as to determine the amount of release-resistant water left by the method (e.g., systems can comprise scales for performing such weighing).

In certain embodiments, the system further comprises a fracture-creating/opening component that is configured to introduce fractures and/or increase the size of fractures (or similar structures) in samples to promote the detection and/or release of release-resistant water in or released from the samples. The fracture-inducing/increasing component can be any suitable component for causing such disruptions in the material to be analyzed. The disruptions should typically not be great enough to disrupt hermetically sealed liquids contained in the samples, such as intact fluid inclusions. Thus, for example, the component can be configured to perform limited freeze-thaw, wherein the temperature, time, both, and/or other conditions of the freeze-thaw are not so great as to cause detectably or significant rupture of hermetically sealed liquids in the material but is strong enough to detectably enhance the release and/or detection of release-resistant water and/or to detectably increase the size and/or amount of microfractures or similar release-resistant water-associated structures in the material. The fracture creating/inducing component can also or alternatively comprise a specialized drill bit configured to generate more fractures in samples, Such drill bits, which can comprise appendages and/or other components for inducing the creation and/or growth of such microfractures are another aspect of the invention. Any of the methods of the invention described above also can comprise the performance of steps that are counterparts of these disclosures relating to components of systems.

The systems described herein can be surprisingly simple and an aspect of the invention is in what is lacking from such systems, in addition to the components that make the system work (and their operation). For example, according to embodiments the invention provides systems having any combination of the preceding features, wherein the system can be characterized in that it lacks a gas chromatography component, lacks a mass spectrometer component, lacks a gamma ray detector component, or lacks any or all thereof.

According to embodiments, a system of the invention includes a component for associating release-resistant water data associated with samples analyzed by the device with other analytical data for samples obtained from a comparable location of a geologic unit under study, such as a petroleum exploration or production site, obtained by other analytical methods, including wire log data, fluid inclusion analysis data, released volatiles data from cuttings according to the '031 application, other standard geologic data (such as that shown in FIGS. 1-3 or disclosed in the '031 application), or a combination of any or all thereof, and for relaying such data to an analyst, such as an operator directing drilling in a petroleum exploration or production operation.

Exemplary Device/System

An exemplary device/system according to particular aspects of the invention is illustrated in FIGS. 6A-6C. To better illustrate the device and method aspects of the invention, the features and operation of this device will now be discussed, with occasional reference made to possible alternative embodiments.

At least a portion of the device will be in contact with the flow line associated with a well. The flow in the flow line comprises drilling cuttings carried in drilling mud.

The drilling mud and cuttings particles from the drilling operation (#2) flow through a strainer (#3A) that is similar to a normal kitchen strainer, although other shapes and configurations of such a material capture component also can be suitably used in the methods of the invention. Drill cuttings and some mud is retained in the strainer, but most of the mud (#4) continues onto the mud surface (#6A) in the Possum Belly (#5A) through the holes in the Strainer (#3A).

Only a small amount of time, less than about 30 seconds, and possibly as short as 5 seconds or less, is needed to capture a sufficient quantity of cuttings for analysis as a sample in the context of this invention, which is expected to be about 0.5 milliliters of material.

The strainer (#3A) is then automatically relocated over another part of the drilling operation Possum Belly (#5B) away from the Flowline (#1). Drilling mud is washed off the sample with a water shower (#8) from a hose and nozzle or shower head (#7) positioned above the sample. The water flow (#8) drains into the Possum Belly (#5B) with the washed off mud onto the mud surface (#6B) in the Possum Belly (#5B). After a short but sufficient time, typically expected to be about 5-15 seconds, the water flow (#8) is shut off and the rinsed cuttings (#11) in the strainer (#3B) are dried by a flow of unheated or slightly heated air (#10) from an air gun (#9) or another drying device. The well site pneumatic air system (not shown) can be utilized for powering the air gun or other drying device.

After sufficient time to dry the sample, possibly about 1 minute (e.g., about 30 seconds-2 minutes), the Strainer (#3C) is relocated to another nearby location which is not over the Possum Belly (#5A and #5B). The Strainer is now positioned over the water saturation analytical device. The surface-dried cuttings particles (#12) are dropped from the Strainer (#3C) into a funnel (#13), which is the entry port into the analytical device. The number of cuttings in the Strainer can be controlled by vents in the funnel at the appropriate height to allow cuttings in excess of that desired for analyses, e.g., about 0.5 milliliters, to be discarded into a discarded sample dump (#29).

At the base of funnel (#13) is an entry valve (#14) that at the appropriate time is opened to allow the cuttings particles to be dumped into the adjacent crushing and pump-down chamber (#15). Before entry valve (#14) is opened the valve on the bottom of the crushing and pump down chamber (#15), valve (#21) is first closed to seal the bottom of chamber (#15) and to arrest the cuttings particles (#12) in the appropriate position to be crushed. Some force may be required (e.g., some force may need to be applied) to help move the cuttings particles from the funnel (#13) into chamber (#15). Entry Valve (#14) is then closed to seal the crushing and pump down chamber (#15).

The cuttings particles (#12) are crushed in this chamber by impact from a ram assembly (#18) having motion transmitted by a means that is suitable to maintain vacuum in the chamber such as bellows (#19) shown in FIG. 6C. The motion and force use to engage and crush the samples can be sourced using an air bellows (#19) as shown, or some other device capable of generating linear motion and applying pressure. After the cuttings sample is crushed, the air cylinder (#20) is retracted by retracting the ram assembly (#18) and re-expanding the bellows (#19). All these processes can be and typically will be automated.

After the cuttings samples is crushed, and with both valve (#14) and valve (#21) sealed shut, then valve (#16) to the vacuum pump (#17) is opened and the pressure in the crushing and pump down chamber (#15) is reduced to below about 20 millibars down to about 2 millibars.

When a pressure about 2 millibars is achieved, valve (#21) is opened to cause the crushed cuttings particles to fall into the analytical chamber (#22). Some force can be required, (e.g., some force may need to be applied) to help remove the crushed cuttings particles from chamber (#15) to analytical chamber (#22).

The analytical chamber (#22) is pumped by vacuum pump (#24) through vacuum valve (#23) to a pressure of less than about 2 millibars before the crushed cuttings sample is dropped from chamber (#15) into the analytical chamber (#22). Both valves (#21) and system exit valve (#28) are closed and the chamber is sealed and the chamber holds no sample within while valve (#23) is open to Vacuum Pump (#24).

The analytical chamber (#22) is heated by electric heating coil (#27) at a constant temperature. This temperature can vary, but typically will be warm enough to encourage rapid discharge of water held tightly in micro cracks and elsewhere in the crushed and evacuated cuttings samples, but not so hot as to cause intact fluid inclusions to decrepitate, or to cause the breakdown of hydrous minerals such as clays or gypsum. Gypsum, fully hydrated calcium sulfate, has a low dehydration temperature at atmospheric pressure of about 98 degrees centigrade. As such, the temperature in the analytical chamber (#22) is typically kept lower than 98 degrees centigrade, such as below about 95 degrees C. An optimum temperature in many embodiments can lie between about 50 to about 75 degrees centigrade. The temperature of the analytical chamber (#22) typically will be held as constant as possible during a single analytical session, and best practice would be maintaining the same temperature on all wells that are analyzed to aid in the comparability of results.

Before valve (#21) is opened to drop the crushed cuttings from chamber (#15) into analytical chamber (#22) vacuum valve (#23) to vacuum pump (#24) is closed. After closing valve (#23), valve (#21) is opened to drop the crushed samples from chamber (#15) to the analytical chamber (#22). Valve (#25) to water meter (#26) has typically remained closed up to now. Valve (#21) is immediately closed after the crushed cuttings samples have dropped from chamber (#15) to analytical chamber (#22). The elevated temperature and reduced pressure in the analytical chamber will exert sufficient force of the crushed and dehydrated cuttings for them to emit their tightly held (release-resistant) water. Valve (#25) is now opened to allow the now released connate water (release-resistant water) that had been tightly confined in the cuttings samples to enter into water meter (#26) and be analyzed, the data being immediately transmitted to those responsible for steering the drilling well.

After the tightly held connate water (i.e., release-resistant water) has been analyzed, valve (#25) to water meter (#26) is closed and the water meter is reconditioned to receive the next sample.

The water meter (#26) can be any of a number of effective devices or technologies, including mass spectrometry, mass measurement of a desiccant, colorimetric analyses of a desiccant that changes color with water content, a resistance-based humidity meter, capacitance manometer, or other appropriate water analytical technology or device.

After valve (#25) to water meter (#26) is closed system exit valve (#28) is opened to discard the analyzed samples along with other discarded cuttings samples (#29). Some force can be required (e.g., some force may need to be applied) to remove all of the old sample from analytical chamber (#22) to the holding place of discarded samples (#29).

After the analyzed sample has been discarded valve (#28) is closed, and vacuum valve (#23) is open to vacuum pump (#24) to recondition the analytical chamber (#22) for the next sample.

The device typically is fully automated and ready to analyze the next sample as soon as the last sample is finished. To speed up analytical time the various processes can be running at the same time on a series of samples. This detailed description of exemplary devices/systems is meant to illustrate with detail the features and operation of particular embodiments, but should not in any way be construed as limiting the overall scope of the invention. The specific exemplary components and functions described herein can be modified in accordance with any other portions of this disclosure or combined with any features/components described elsewhere herein or used in performing steps of methods described elsewhere herein.

Computer Implemented Aspects

In another aspect, the invention provides systems and methods that utilize computerized devices/systems in the performance of the methods described herein, that utilize information generated in the performance of methods described herein, or both. For example, in one aspect the invention provides a computer-implemented method or system that comprises a computerized device or system comprising instructions for the control of devices/systems that perform the step of analyzing sensor data associated with release-resistant water in a mater and that further optionally control devices/systems associated with the steps of removing extraneous water from material, extracting release resistant water from material, or both. Such and other computerized systems provided by this disclosure will comprise a memory component/system comprising persistent, transferrable, and reproducible computer/processor readable/writable media (e.g., non-transient computer readable/writable media) that contains one or more engines/programs comprising preprogrammed steps for relaying signals to control the operation of such devices; preprogrammed conditions for automatically triggering operation of such devices, relaying messages to users, and the like; conditions for receiving and relaying information to users through user interfaces (e.g., over the internet, such as over secure internet communication channels), messages to mobile/remote computing devices, etc.; and optionally the ability to store data (e.g., recoding sensor information and associated material information in electronic records/data), and optionally analyze recorded data (optionally in combination with related data, received user input, or both), concerning the performance of such devices/systems, steps, etc., in combination with processor(s) for reading and implementing such instructions/engines and data, performing such analyses, generating output, and relaying output (e.g., applications sent to mobile clients from a server, such as mobile device applications). In aspects, such data is combined with other data, e.g., from performance of other methods, such as conventional well logging and in aspects such data or combined data is stored in one or more data repositories, such as one or more relational databases. In aspects, any such data is analyzed against preprogrammed conditions and used to control operation of drilling equipment, fracking operations, and the like, or to send reports, messages, recommendations, and the like to operators of such equipment. In aspects, such computer information includes information from sites that are related in one or more aspects (e.g., formation, depth, etc.), which is compared against information for a current site/area, etc. In aspects, such data can provide a model for recommending additional sites for drilling/exploration. In aspects, methods include providing such information to a machine learning/artificial intelligence model or set of models and employing the model to make recommendations about additional production, drilling, or exploration activities. In aspects, the use of computer-implemented methods/systems provided as such allow for one or more of automatic loading of materials, removal of extraneous water, preparing materials (e.g., by crushing), extraction of release resistant water (e.g., by automatic application of pressure in response to preprogrammed condition(s), such as the presence of sufficiently dry material), application of in situ release water measurement methods (e.g., automatically in response to preprogrammed condition(s)), operation of sensor(s) to measure extracted/release release-resistant water (automatically based on preprogrammed conditions such as the presence of a certain amount of liquid/humidity), reading of sensor data, analysis of sensor data, relay of sensor data, relay of analytical data, or associated control of physical devices, such as steering or other operation of drilling devices, etc. Computerized systems for performing the analysis of data, storing data, relaying data, receiving data, and displaying data, are well known in the art, and need not be described herein in detail. The invention also provides systems/devices comprising computerized systems that perform such functions described in this section, e.g., in controlling the analysis of sensor-detected release resistant water in a material, analyzing it, and reporting on it, such analysis, or both, optionally further controlling the operation of one or more devices/systems networked therewith. In aspects, such aspects can be described as "steps for performing" such functions or "means for performing such functions," recognizing, again, that while such conventional processing, memory, and engine aspects are well described in the art such that there are numerous known equivalents for the general means/steps described for such methods/systems described herein. In aspects, any of the above-described steps of the method in this disclosure are performed by a computer-implemented controller that performs one, some, most, or all of such steps in response to one or more preprogrammed instructions/conditions, computer-generated instructions/conditions (e.g., in the case of machine learning aspects), or both, relating to the timing or conditions of the performance of such steps.

EXEMPLARY APPLICATIONS OF METHODS OF THE INVENTION

The following examples of the application of methods of the invention further illustrate various aspects of the invention but should not be construed as in any way as limiting the scope of the claims or the rest of the disclosure provided herein.

Example 1

This Example demonstrates the use of (some of) the methods of the invention to determine water saturation in a geological site based on analyses of cuttings taken from a petroleum well, and identification of oil pay zones through application of the inventive method on the petroleum well cuttings.

One hundred and fifty (150) petroleum drill cuttings samples were collected from a first vertical petroleum well drill site, washed and gently dried, bagged at the well, and upon reaching the laboratory were placed into a device described by U.S. Pat. App. 2018/0306031. The samples were subjected to pressure conditions of 20 millibars at room temperature for 7.5 minutes such that removal of extraneous water occurred.

Once the extraneous water was removed, the remaining sample was subjected to pressure conditions of 2 millibars at room temperature for 7.5 minutes such that the resistant water located in the microfractures was released in the form of a gas. The gas was subjected to mass spectrometry and the results are presented in FIG. 1.

Figure 1:
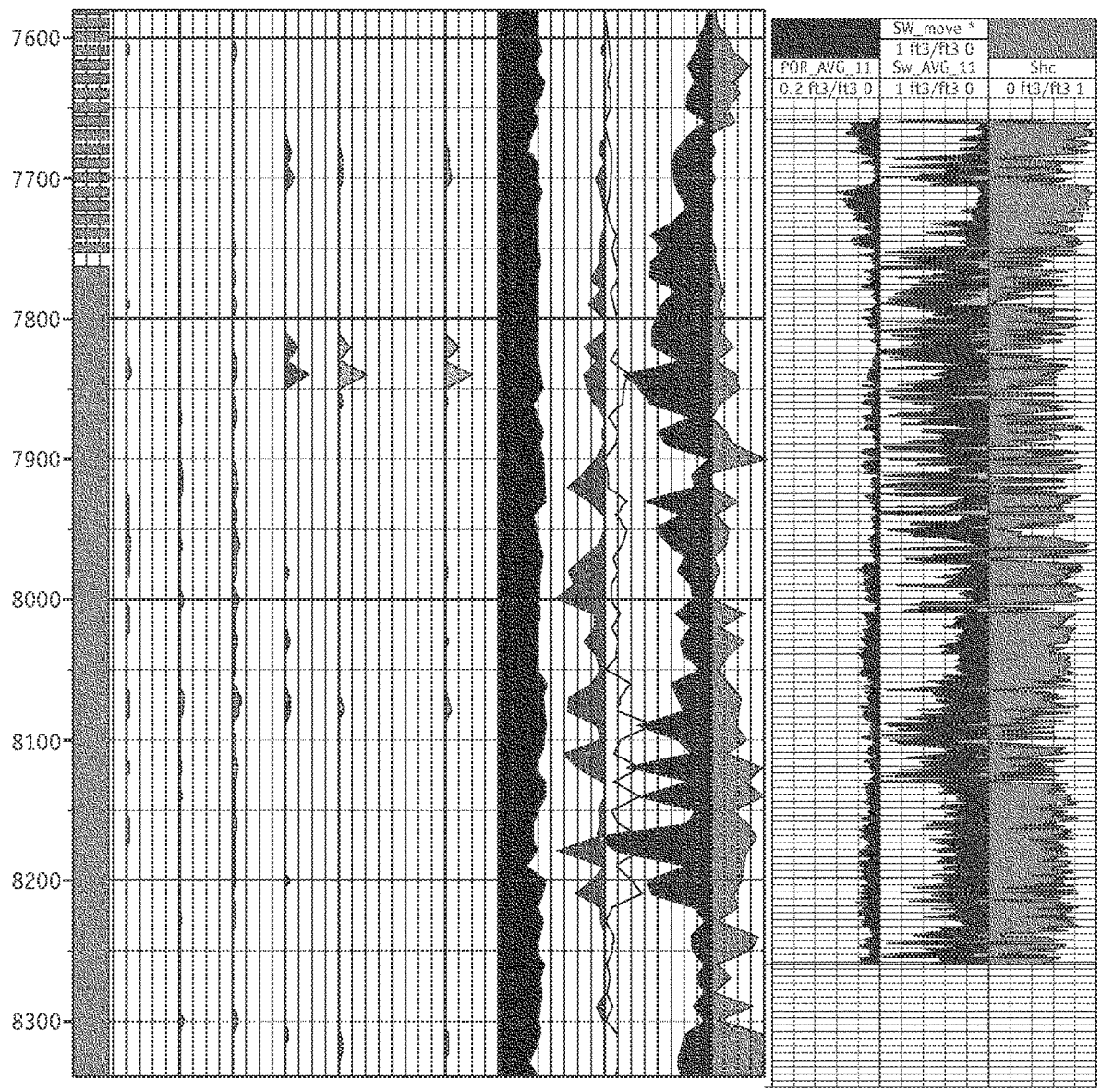
FIG. 1 is a plot of a data obtained from running an exemplary method of the invention on a number of drill cuttings obtained from a first vertical petroleum well which provides a visual comparison between water saturation curves derived from performing methods of the invention on the cuttings and petrophysical data derived from wire line logs.

Overlain on the top of FIG. 1 are three columns of petrophysical data derived from wire line logs. From left to right, the petrophysics derived parameters are porosity, Sw, and Hydrocarbon Saturation, or S-hydrocarbon.

Immediately to the left of the overlain petrophysical data, the plot labeled "Water" shows water saturation (Sw) results from applying the methods of the current invention to the cuttings described above. The data plot identifies areas of relatively low- or high-water content, which in turn show where oil is located in the site. The shaded area in the water column of FIG. 1 demonstrates a prominent pay zone, and this area correlates with the shaded petrophysical Sw defined pay zone identified in the overlaid columns.

Numerous additional data points were also obtained and are reflected in FIG. 1 based on application of the methods of the '031 application (e.g., formic acid). This demonstrates how the release-resistant water analysis method of the invention can be used in coordination with the analytical methods described in the '031 application (e.g., rock volatiles stratigraphy).

Example 2

This Example demonstrates another use of the methods of the invention to determine water saturation in a geological site based on analyses of cuttings taken from a petroleum well, and identification of oil pay zones through application of the inventive methods on the drill cuttings.

Two hundred (200) cuttings were collected from a second vertical petroleum well drill site, washed and gently dried, bagged at the well, and upon reaching the laboratory were placed into an analytical device described by U.S. Pat. App. 2018/0306031. The samples were subjected to pressure conditions of 20 millibars at room temperature for 7.5 minutes until removal of extraneous water had occurred.

Once the extraneous water was removed, the remaining sample was subjected to pressure conditions of 2 millibars at room temperature for 7.5 minutes such that the resistant water located in the microfractures was released in the form of a gas. The gas was subjected to mass spectrometry and the results are presented in FIG. 2.

Figure 2:
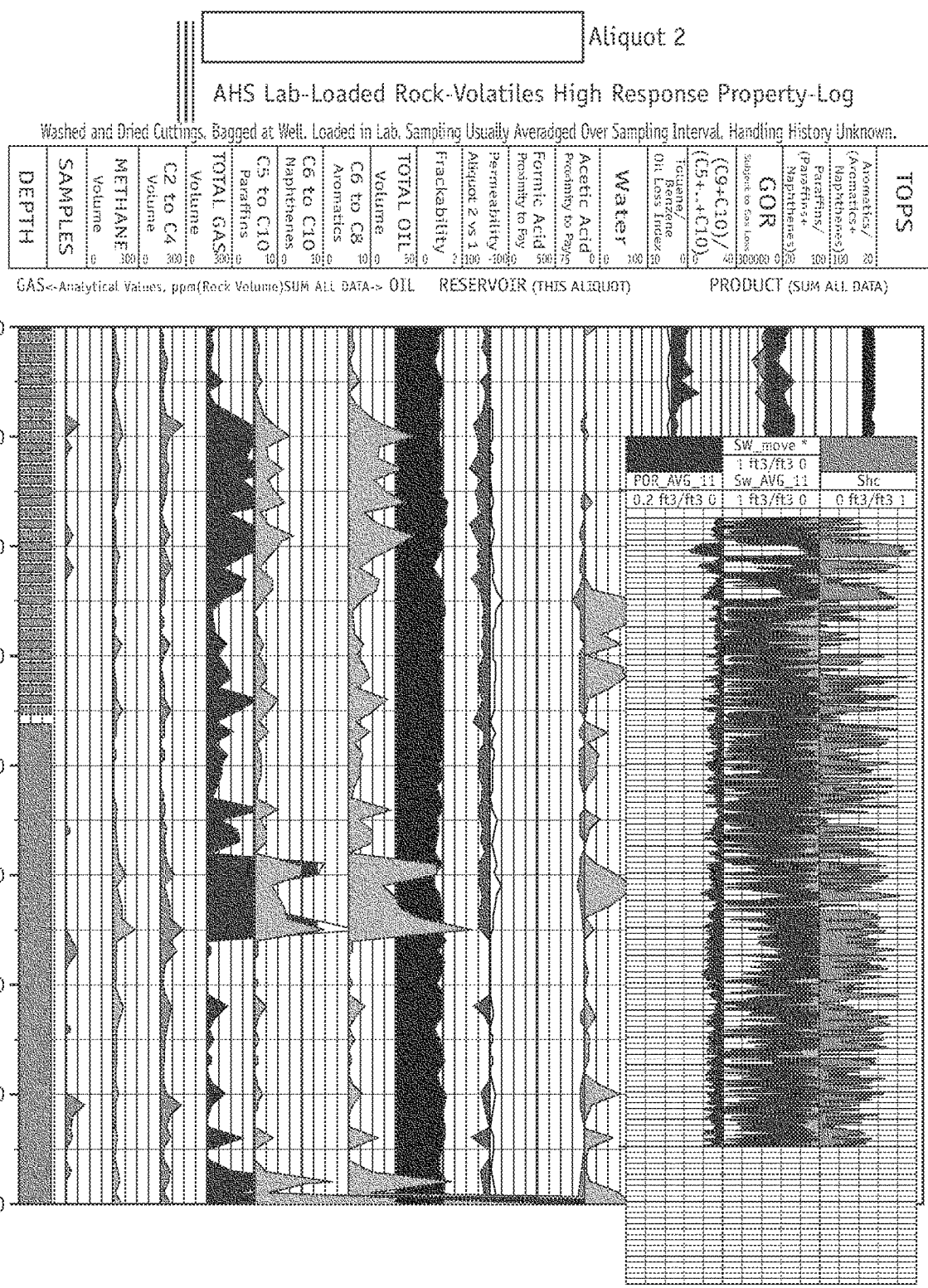
FIG. 2 is a second plot of data from performing an exemplary method of the invention on a number of drill cuttings obtained from a second vertical petroleum well which provides a visual comparison between water saturation curves derived from performing methods of the invention on the cuttings and petrophysical data derived from wire line logs.

Overlain on the top of FIG. 2 are three columns of petrophysical data derived from wire line logs. From left to right, the petrophysics-derived parameters are porosity, Sw, and Hydrocarbon Saturation, or S-hydrocarbon.

Immediately to the left of the overlain petrophysical data, the plot labeled "Water" shows water saturation (Sw) results from applying the methods of the current invention to the cuttings described above. The data plot identifies areas of relatively low- or high-water content, which in turn show where oil is. The shaded area in the water column of FIG. 1 demonstrates a prominent pay zone, and this area correlates with the shaded petrophysical Sw defined pay zone identified in the overlaid columns. Again, additional data points secured through the performance of methods described in the '031 application also are included in the data.

Example 3

This Example demonstrates the use of a method of the invention to determine water saturation in a geological site based on analyses of cuttings taken from a petroleum well, and identification of oil pay zones through application of the inventive method on the cuttings.

Four hundred (400 cuttings) were collected from a horizontal petroleum well site, the well drilled using oil-based mud. The cuttings were washed and gently dried, bagged at the well, and upon reaching the laboratory were placed into a device described by U.S. Pat. App. 2018/0306031. The samples were subjected to pressure conditions of 20 millibars at room temperature for 7.5 minutes until removal of extraneous water had occurred (the method was performed on samples in cylindrical containers with a diameter of about 0.25 inches and a length of about 3.25 inches as discussed elsewhere herein and in the '031 application).

Once the extraneous water was removed, the remaining sample was subjected to pressure conditions of 2 millibars at room temperature for 7.5 minutes such that the resistant water located in the microfractures was released in the form of a gas. The gas was subjected to mass spectrometry and the results are presented in FIG. 3.

The column $7^{th}$ from the right, labeled "Water" shows water saturation (Sw) results from applying the methods of the current invention to the cuttings described above. The data plot identifies areas of relatively low- or high-water content, which in turn indicate where oil is.

Figure 3:
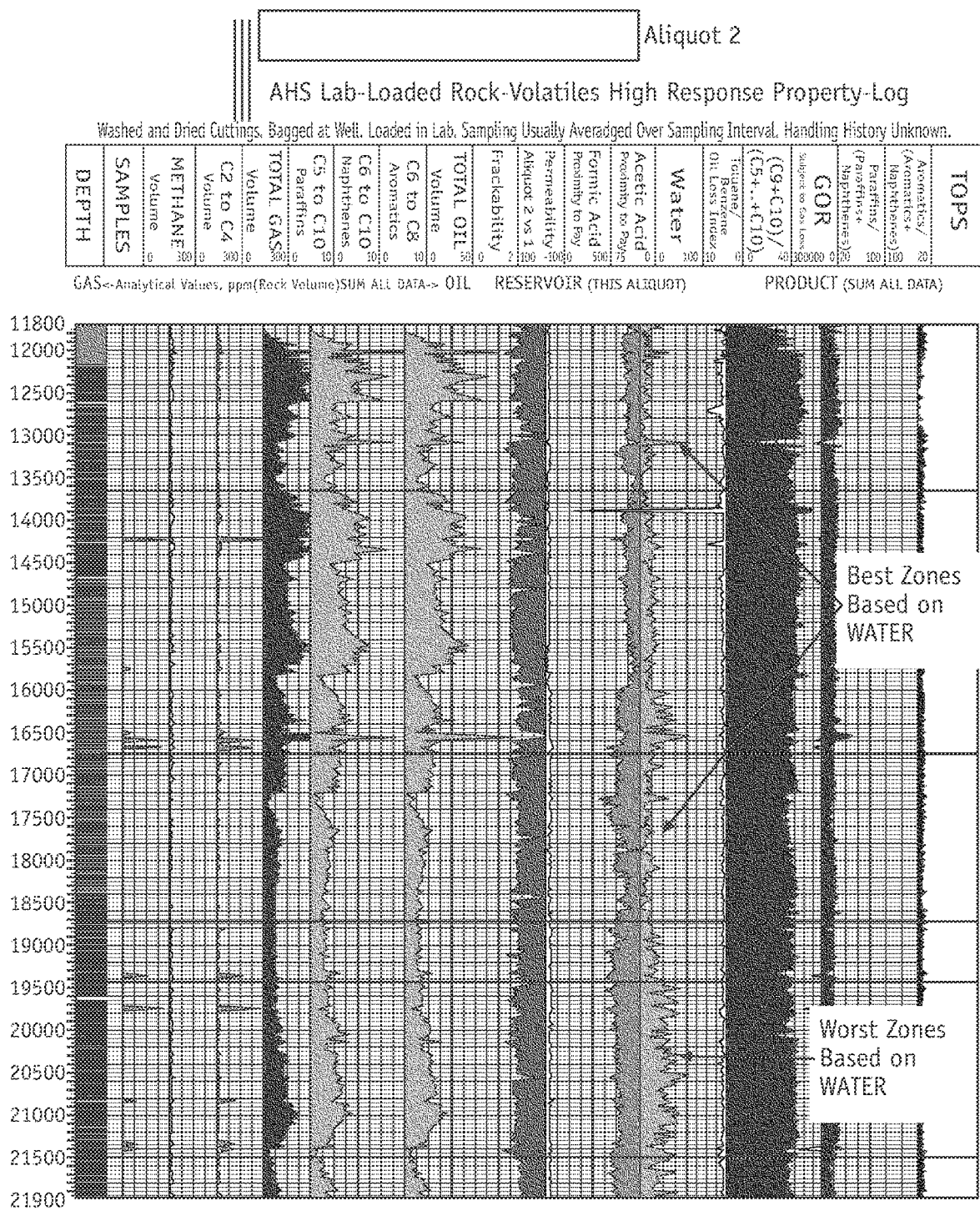
FIG. 3 is a plot of data obtained from performing a method of the invention on cuttings obtained from a horizontal petroleum well.

Numerous additional data points were also obtained and are reflected in FIG. 3, such as formic acid, acetic acid, etc., derived from the volatiles analysis method of the '031 application. The shaded area in the water plot demonstrates a prominent pay zone, and this area correlates with the shaded defined pay zones identified in additional data plots of FIG. 3.

EXEMPLARY ASPECTS OF THE INVENTION

A non-limiting list of exemplary aspects, embodiments, and features of the invention is provided here to better illustrate the scope of the invention and possible combinations of the recited elements described above.

In an aspect (aspect 1), the invention provides a method for analyzing the amount of release-resistant water associated with a material comprising (a) placing a material in an enclosure such that the material is isolated from the environment; (b) removing substantially all (i.e., at least substantially all) of the extraneous water associated with the material, (c) removing substantially all of the released extraneous water from the enclosure; (d) applying an extracting force to the sample of material in the enclosure, wherein the extracting force is capable of causing the release of a detectable amount release-resistant water from the material if present, and (e) measuring the amount of release-resistant water released from the material through the performance of step (d).

In aspects, the invention provides the method of aspect 1, wherein the extracting force optionally means the combination of two or more forces; the extracting force is about equal in effectiveness in terms of removing release-resistant water to application of a vacuum at a pressure of about 2 millibars for a period of less than about 9 minutes; and wherein the conditions of the method are such that no more than 1% of the crystalline minerals present in the composition decompose and release their structural water in the performance of the method (aspect 2).

In aspects, the invention provides the method of aspect 1 or aspect 2, wherein the extracting force causes release-resistant water in the material to evaporate and to form water vapor and step (e) comprises directly or indirectly measuring water in the water vapor (aspect 3).

In aspects, the invention provides the method of aspect 3, wherein the extracting force is at least predominately comprised of a vacuum pressure of about 2 millibars, which is optionally applied for a period of less than about 9 minutes, and wherein application of the vacuum is optionally performed at about room temperature (about 18-about 28 degrees C., more typically about 20-about 25 degrees C.) (aspect 4).

In aspects, the invention provides the method of aspect 3 or aspect 4, wherein the step of measuring the water in the water vapor is carried out by measuring one or more compounds that are indirectly indicative of the amount of water present in the evaporated release-resistant water (aspect 5).

In aspects, the invention provides the method of any one of aspects 1-5, wherein the step of measuring the release-resistant water in the sample comprises subjecting water vapor formed from the release-resistant water to mass spectrometry analysis (aspect 6).

In aspects, the invention provides the method of aspect 6, wherein the step of measuring the release-resistant water is performed by analyzing the content of one or more elements or compounds formed from the release-resistant water and that are indicative of the amount of release-resistant water in the material, such as hydrogen ($H_2$), formed in subjecting water vapor generated from the release-resistant water to mass spectrometry (aspect 7).

In aspects, the invention provides the method of any one of aspects 1-5, wherein step (e) comprises measuring the release-resistant water by application of a humidity meter, measurement of the difference of mass in the media before and after application of removal/extraction, use of a capacitance manometer, or a combination of any or all thereof (aspect 8).

In aspects, the invention provides the method of any one of aspects 1-5, wherein step (e) comprises measuring the release-resistant water by application of a chemical assay (aspect 9).

In aspects, the invention provides the method of aspect 9, wherein step (e) of the method comprises contacting the release-resistant water released from the material with an absorbent and measuring a mass change or a chemical change (e.g., a color change) in the absorbent (e.g., by application of color-indicating Drierite™) (aspect 10).

In aspects, the invention provides the method of any one of aspects 1-10, wherein the method further comprises the step of trapping and concentrating the release-resistant water with a trapping media to generate an aliquot of resistant water that is subjected to analysis (which optionally is in water vapor form when trapped and/or released from the trap) (aspect 11).

In aspects, the invention provides the method of any one of aspects 1-11, wherein the step of removing the extraneous water comprises application of one or more initial forces that causes the release of a first gas from the material, wherein the one or more initial forces are capable of causing substantially all extraneous water, if present, to evaporate, and the method comprises removing the first gas from the enclosure (aspect 12).

In aspects, the invention provides the method of aspect 12, wherein the one or more initial forces comprises application of a vacuum at a specific pressure and temperature applied to the material to remove substantially all of the extraneous water while leaving a detectable amount of release-resistant water in the material (aspect 13).

In aspects, the invention provides the method of aspect 12 or aspect 13, wherein the one or more initial forces comprises application of a vacuum applied at about 20 millibars for a period of less than about 9 minutes (aspect 14).

In aspects, the invention provides the method of aspect 14, wherein the one or more initial forces is applied at about room temperature (about 18-about 28 degrees C., more typically about 20-about 25 degrees C., such as about 22-24 degrees C.) (aspect 15).

In aspects, the invention provides the method of aspect 14 or aspect 15, wherein the one or more initial forces is applied for between about 7 minutes and about 8 minutes or between about 1 minute and about 6 minutes, such as about 1.5 minutes to about 4.5 minutes (aspect 16).

In aspects, the invention provides the method of any one of aspects 1-11, wherein the step of removing the extraneous water is performed by bringing the material into contact or operable association with a water absorbing material (aspect 17).

In aspects, the invention provides the method of any one of aspects 1-17, wherein the method does not comprise exposing the material to an oven or other high heating source (e.g., the maximum temperature in performing the method is less than about 100 degrees C., less than about 95 degrees C., or less than about 80 degrees C.), does not comprise freezing the material, does not comprise subjecting the release-resistant water or any water vapor formed therefrom to gas chromatography, or does not include a combination of any or all thereof (aspect 18).

In aspects, the invention provides the method of any one of aspects 1-18, wherein the extracting force comprises application of a vacuum under pressure and temperature conditions that cause the release of a detectable amount of release-resistant water as water vapor (aspect 19).

In aspects, the invention provides the method of aspect 19, wherein the extracting force comprises application of a vacuum at about 2 millibars for a period of less than about 9 minutes (aspect 20).

In aspects, the invention provides the method of aspect 20, wherein the extracting force is applied at room temperature (aspect 21).

In aspects, the invention provides the method of aspect 20 or aspect 21, wherein the extracting force is applied for between about 7 and about 8 minutes, between about 1 minute and about 6 minutes, between about 1.5 minutes and about 4.5 minutes, or between about 2 minutes and about 4 minutes (aspect 22).

In aspects, the invention provides the method of any one of aspects 1-22, wherein the method does not comprise analyzing hydrocarbons or organic compounds present in the release-resistant water (e.g., the method does not comprise any measurement of oil-saturated water) (aspect 23).

In aspects, the invention provides the method of any one of aspects 1-23, wherein the material is mechanically disrupted in the enclosure by application of a mechanical disrupting force that directly or indirectly disrupts the material under conditions wherein at least a detectable amount of release-resistant water in the material is not lost (aspect 24).

In aspects, the invention provides the method of aspect 24, wherein the mechanical disrupting force is applied prior to step (b) of the method (aspect 25).

In aspects, the invention provides the method of aspect 24 or aspect 25, wherein the mechanical disrupting force is applied directly to the enclosure, at least part of the disruption of the enclosure is transmitted to the material, and at least substantially none of the release-resistant water in the material is lost in the process of disrupting the enclosure (suitable devices, systems, and methods for such indirect crushing of material, such as cuttings, are described in connection with the release of volatile compounds from cuttings in the '031 application) (aspect 26).

In aspects, the invention provides the method of any one of aspects 1-26, wherein the material is not subjected to mechanical disruption outside of the enclosure or an environment that would maintain a detectable amount of release-resistant water in the sample prior to the performance of step (b) of the method (e.g., where the material is a collection of cuttings the cuttings are collected before contact with a shaker table) (aspect 27).

In aspects, the invention provides the method of any one of aspects 1-27, wherein prior to performing analysis on the release-resistant water content of the material, one or more steps are performed that increase the release of release-resistant water in the material but do not rupture hermetically sealed fluid-containing structures, such as fluid inclusions, contained in the material (e.g., the method comprises the use of specially-designed drill bits to induce creation of and/or increase of size of microfractures in the material and/or the use of freeze-thawing of the material to induce creation of and/or increase of size of microfractures in the materials, thereby promoting release of release-resistant water in the method) (aspect 28).

In aspects, the invention provides the method of aspect 1, wherein the material is not subjected to the extracting force of step (d) causing the release of release-resistant water; and wherein the amount of release-resistant water in step (e) is measured without such release-resistant water being extracted or otherwise released from the material, i.e. while the release-resistant water is within the material (or "in-situ") (aspect 29).

In aspects, the invention provides the method of aspect 29 wherein the method further comprises any of the steps of aspects 1, 6-18, or 23-27 and wherein the release-resistant water is measured in-situ such that the in-situ method would not require the extraction of the release-resistance water from the material, comprising, for example, capacitance manometry, thermal gravimetric analyses, differential scanning calorimetry, spectroscopic methods such as NMR, MM, Raman spectroscopy, and Infrared Spectroscopy, as well as methods comprising weighing the material prior to and after removal of the extraneous water (aspect 30).

In aspects, the invention provides the method of any one of aspects 1-30, wherein the method further comprises obtaining a number of samples of material from different parts of a geologic unit and performing steps (a)-(e) on each one of the samples (whether step (e) is applied in-situ or on extracted release-resistant water), wherein the relative amount of release-resistant water measured in each cycle from each sample is used to generate a map of one or more properties of the geologic unit derived from the measurements of release-resistant water (aspect 31).

In aspects, the invention provides the method of aspect 31, wherein the geologic unit is a petroleum site, the samples are petroleum drill cuttings, and wherein release-resistant water does not include water hermetically sealed in fluid inclusions in the cuttings during steps (b)-(e) of the method (aspect 32).

In aspects, the invention provides the method of aspect 31 or aspect 32, wherein the samples are petroleum drill cuttings and the amount of water released from fluid inclusions due to disruption of the material makes up less than about 50% of the release-resistant water (aspect 33).

In aspects, the invention provides the method of aspect 33, wherein the amount of water released from fluid inclusions makes up less than about 10% of the release-resistant water (aspect 34).

In aspects, the invention provides the method of any one of aspects 31-34, wherein the samples are petroleum drill cutting obtained from a horizontal petroleum well (aspect 35).

In aspects, the invention provides the method of aspect 35, wherein at least about 85% of the horizontal petroleum well was contained with a vertical zone of about 10 feet or less (aspect 36).

In aspects, the invention provides the method of any one of aspects 31-36, wherein the relative amount of water identified in the samples are used as an index of water saturation (Sw) and therefore can be used to locate oil and gas pay zones (aspect 37).

In aspects, the invention provides the method of aspect 37, wherein the method is performed along with other analytical methods that characterize the geological properties of the geological unit or geological site (such as ductility, hardness, permeability, and/or porosity), the amount and/or location of oil present in the geological unit, e.g., site, or both (e.g., conventional well logging, fluid inclusion analysis, core analysis, etc.) (aspect 38).

In aspects, the invention provides the method of any one of aspects 31-38, wherein the samples are obtained from a low visibility site, such as a freshwater petroleum exploration or well site (aspect 39).

In aspects, the invention provides the method of any one of aspects 31-39, wherein the method is performed within proximity to an exploration site or well site (e.g., within about 0.66 miles, within about 0.33 miles, or within about 0.15 miles of the site) and results are obtained for the analysis of each sample within less than about 10 minutes from capturing the samples from the flow of drilling material on average (aspect 40).

In aspects, the invention provides the method of any one of aspects 31-40, wherein at least steps (a)-(d) of the method are performed with non-sparking components, devices, or materials (aspect 41).

In aspects, the invention provides the method of any one of aspects 31-41, wherein the method comprises a step of washing the samples prior to the performance of step (b) (aspect 42).

In aspects, the invention provides the method of any one of aspects 31-42, wherein the method is performed concurrently with drilling a petroleum well and the results of the method are used to direct the direction or placement of future drilling (i.e., to "steer" the well) (aspect 43).

In aspects, the invention provides a system for analyzing release-resistant water in materials comprising: (a) a collection component capable of capturing samples and delivering samples into an enclosed analytical device; (b) a washing component configured to wash delivered samples in an average time of about 1 minute or less; (c) a drying component capable of removing extraneous water from washed samples in an average time of about 2 minutes or less; and (d) an enclosed device comprising, (i) a sorting component for sorting samples from one another, (ii) a crushing component configured to crush the samples in an average time of about 1 minute or less, and (iii) an analytical component capable of analyzing the amount of release-resistant water in the enclosure (aspect 44).

In aspects, the invention provides the system of aspect 44, wherein the analytical component comprises a device or component that is capable of measuring release-resistant water still contained within samples after the removal of extraneous water (e.g., an MM device, NMR device, or similar device) (aspect 45).

In aspects, the invention provides the system of aspect 45, wherein the analytical component operates by performing methods that would not require the extraction of the release-resistant water from the sample comprising, for example, capacitance manometry, thermal gravimetric analyses, differential scanning calorimetry, spectroscopic methods such as NMR, MM, Raman spectroscopy, and infrared spectroscopy, as well as methods comprising weighing the material prior to and after removal of the extraneous water (aspect 46).

In aspects, the invention provides the system of aspect 44, wherein the enclosed device further comprises (iv) an extraction component capable of exerting a force on the samples capable of extracting an analyzable amount of release-resistant water and wherein the analytical component analyzes release-resistant water released from samples (aspect 47).

In aspects, the invention provides the system of aspect 47, wherein the extraction component can extract an analyzable amount of release-resistant water from samples that the system is configured to analyze in an average time of about 2 minutes or less (aspect 48).

In aspects, the invention provides the system of aspect 47 or aspect 48, wherein the extraction component comprises a vacuum-generating component capable of generating a vacuum that when applied can extract a detectable amount of release-resistant water from samples the device is configured to operate on (aspect 49).

In aspects, the invention provides the system of aspect 49, wherein the extraction component comprises both a heating component and a vacuum component, which can work independently and/or in concert to extract release-resistant water from the samples (aspect 50).

In aspects, the invention provides the system of aspect 48 or aspect 50, wherein the system comprises a first selectively and/or automatically operable valve for controlling the application of force generated by vacuum-generating component on the samples and/or release-resistant water and a second selectively and/or automatically operable valve for controlling flow of release-resistant water to the analytical component (aspect 51).

In aspects, the invention provides the system of any one of aspects 44-51, wherein the enclosed device comprises a first chamber containing the crushing component and a separate second chamber comprising the extraction component and that comprises or is in communication with the analytical component, wherein samples are capable of flowing from the first chamber to the second chamber under automated or selectively controlled conditions (aspect 52).

In aspects, the invention provides the system of any one of aspects 44-52, wherein the collection component comprises channels for permitting the passage of a flow of liquid containing solid samples (aspect 53).

In aspects, the invention provides the system of any one of aspects 44-53, wherein the enclosed device comprises one or more gating components, one or more tortuous path components, or both, to control the flow of samples through the enclosed device (aspect 54).

In aspects, the invention provides the system of any one of aspects 44-54, wherein the system comprises a mechanism for moving the collection component from contact with a flow of material comprising material to be collected as samples to the enclosed device (aspect 55).

In aspects, the invention provides the system of any one of aspects 44-55, wherein the system comprises a discarding component for selectively and/or automatically removing analyzed samples from the system (aspect 56).

In aspects, the invention provides the system of any one of aspects 44-56, wherein at least some of the components of the system, including the crushing component, are configured to be powered by a petroleum well pneumatic power system (aspect 57).

In aspects, the invention provides the system of any one of aspects 44-57, wherein the system further comprises a communication component for relaying data obtained from the analytical component to a well site operator and programmable controls for operating most or all operations of the system (aspect 58).

In aspects, the invention provides the system of any one of aspects 44-58 wherein the system further comprises a fracture-creating/opening component that is configured to introduce fractures and/or increase the size of fractures (or similar structures) in samples to promote the detection and/or release of release-resistant water in or released from the samples (aspect 59).

In aspects, the invention provides the system of aspect 59, wherein the fracture-opening component comprises a component that causes fractures through freeze-thaw (aspect 60).

In aspects, the invention provides the system of aspect 59, wherein the fracture creating/inducing component comprises a specialized drill bit configured to generate more fractures in samples (aspect 61).

In aspects, the invention provides the system of any one of aspects 44-61, wherein the system lacks a gas chromatography component, lacks a mass spectrometer component, lacks a gamma ray detector component, or lacks any or all thereof (aspect 62).

In aspects, the invention provides the system of any one of aspects 44-62, wherein the system includes a component for associating release-resistant water data associated with samples analyzed by the device with other analytical data for samples obtained from a comparable location of a geologic unit, such as a petroleum exploration or production site, obtained by other analytical methods, including wire log data, fluid inclusion analysis data, released volatiles data from cuttings according to the '031 application, other standard geologic data (such as that shown in FIGS. 1-3 or disclosed in the '031 application), or a combination of any or all thereof, and for relaying such data to an analyst, such as an operator directing drilling in a petroleum exploration or production operation (aspect 63).

In aspects, the invention provides a method for analyzing a material containing release-resistant water comprising: (a) removing at least about 99% of any water associated with the material that is removable from the material by subjecting the material to a temperature of at least about 100 degrees C. water at normal atmospheric pressure ("extraneous water") from the material to obtain extraneous water-free material; (b) applying an extraction force to the extraneous water-free material to release a detectable amount of extractable water that contained in the material after performing step (a) ("release-resistant water"), (c) measuring an amount of release-resistant water released from the material, and (d) using the measurement of the amount of release-resistant water to assess the characteristics of the material (aspect 64).

In aspects, the invention provides the method of aspect 64, wherein the method is repeated two or more times using two or more different materials using the same methods or methods of substantially similar efficacy for the removal of the extraneous water and extraction of the release-resistant water and substantially identical methods of measuring the release-resistant water (aspect 65).

In aspects, the invention provides the method of aspect 65, wherein the material predominately is composed of rock (aspect 66).

In aspects, the invention provides the method of aspect 66, wherein the material is a sample from a geologic unit such as a petroleum well (aspect 67).

In aspects, the invention provides the method of aspect 67, wherein the material is a petroleum drill cutting (aspect 68).

In aspects, the invention provides the method of any one of aspects 64-68, wherein the step of removing the extraneous water comprises physical drying of the material (aspect 69).

In aspects, the invention provides the method of aspect 69, wherein removing the extraneous water further comprises applying an additional extraneous water removal force to the material after physically drying the material (aspect 70).

In aspects, the invention provides the method of aspect 70, wherein the additional extraneous water removal force is selected from applying heat to the material, applying a vacuum to the material, chemically drying the material, or performing a combination of thereof to the material (aspect 71).

In aspects, the invention provides the method of aspect 71, wherein the entire step of removing the extraneous water is performed at a temperature of less than about 100 degrees (aspect 72).

In aspects, the invention provides the method of any one of aspects 64-72, wherein the step of removing extraneous water comprises applying a vacuum to the material (aspect 73).

In aspects, the invention provides the method of aspect 73, wherein the step of removing the extraneous water comprises applying a vacuum force that has at least about the same water removal efficiency/efficacy as applying a vacuum of about 20 millibars to a sample of 300-400 microliters of rock for a period of at least about 5 minutes in a cylindrical container that is impermeable with respect to water, and which has a diameter of about 0.25 inches and a length of about 3.5 inches (aspect 74).

In aspects, the invention provides the method of aspect 70, wherein the step of removing the extraneous water comprises heating the material to a temperature of more than about 100 degrees C. for at least about 30 seconds (aspect 75).

In aspects, the invention provides the method of aspect 75, wherein the step of removing the extraneous water comprises causing the temperature of the water to rise to between at least about 100 degrees C. and about 125 degrees C. for at least one minute (e.g., at least about 100 degrees C. and less than about 115 degrees C., at least about 100 degrees C. and less than about 113 degrees C., about 100-110 degrees C., or about 100 degrees C. and about 105 degrees C.) (aspect 76).

In aspects, the invention provides the method of any one of aspects 64-76, wherein the step of removing the extraneous water does not result in the extraction of more than about 5% of the release-resistant water in the sample at the initiation of the method (aspect 77).

In aspects, the invention provides the method of any one of aspects 64-77, wherein the steps of the method are performed in less than about 5 minutes (aspect 78).

In aspects, the invention provides the method of any one of aspects 64-78, wherein the extraneous water-free material is enclosed during the step of extracting the release-resistant water (aspect 79).

In aspects, the invention provides the method of aspect 79, wherein the step of measuring the extracted release-resistant water comprises using a capacitance manometer to measure at least a portion of the extracted release-resistant water (aspect 80).

In aspects, the invention provides the method of any one of aspects 64-80 wherein the extraction of the release-resistant water comprises applying a vacuum pressure to the extraneous water-free material (aspect 81).

In aspects, the invention provides the method of aspect 81, wherein the vacuum pressure is at least as effective in extracting release-resistant water as applying a vacuum of about 2 millibars to a sample of 300-400 microliters of rock for a period of at least about 5 minutes in a cylindrical container that is impermeable with respect to water, and which has a diameter of about 0.25 inches and a length of about 3.5 inches (aspect 82).

In aspects, the invention provides the method of aspect 82, wherein no more than about 2% of the crystalline minerals present in the composition decompose and release structural water in the performance of the method (aspect 83).

In aspects, the invention provides the method of aspect 83, wherein the step of measuring the release-resistant water in the sample comprises subjecting water vapor formed from the release-resistant water to mass spectrometry analysis (aspect 84).

In aspects, the invention provides the method of aspect 84, wherein the step of measuring the release-resistant water is performed by analyzing the content of one or more elements, ions, or compounds formed from the release-resistant water and that are indicative of the amount of release-resistant water in the material, such as hydrogen ($H_2$), formed in subjecting water vapor generated from the release-resistant water to mass spectrometry (aspect 85).

In aspects, the invention provides the method of aspect 84 or aspect 85, wherein the step of removing extraneous water comprises subjecting the material to a vacuum pressure that extracts a measurable amount of organic volatile compounds in the material, wherein at least about 70% of the organic volatile materials (e.g., at least about 80% of the organic volatile materials, at least about 90% of the organic volatile materials, at least about 95% of the organic volatile materials, at least about 98% of the organic volatile materials, or at least about 99% of the organic volatile materials) were not contained in fluid inclusions (aspect 86).

In aspects, the invention provides the method of any one of aspects 64-86, wherein the step of measuring the release-resistant water comprises measuring water with a humidity meter, application of a chemical assay, calculation of changes in mass of the material, or a combination of any thereof (aspect 87).

In aspects, the invention provides the method of any one of aspects 64-87, wherein the material is mechanically disrupted prior to the extraction of the release-resistant water (aspect 88).

In aspects, the invention provides the method of aspect 88, wherein the material is enclosed when the material is mechanically disrupted, and the material is indirectly disrupted by applying a force on the enclosure (aspect 89).

In aspects, the invention provides the method of aspect 89, wherein the enclosure is a water impermeable, crushable container, the material is a sample of a geologic material, and the material is disrupted by applying one or more forces to the container, the container is crushed without the release of volatile compounds in the container, and the extraction of the release-resistant water is performed at least in part on the material in the container (aspect 90).

In aspects, the invention provides the method of any one of aspects 64-90, wherein the method is performed on at least about 10 samples (e.g., at least about 20 samples, at least about 30 samples, at least about 50 samples, at least about 70 samples, at least about 100 samples, or more, such as about 20-200 samples, about 10-1000 samples, or about 15-1500 samples) obtained from different parts of a petroleum well (e.g., areas separated by each other in at least one dimension by at least about 30 feet, at least about 50 feet, at least about 60 feet, at least about 75 feet, at least about 100 feet, at least about 150 feet, at least about 200 feet, at least about 250 feet, at least about 300 feet, or by a distance of about 20-200 feet, about 30-300 feet, about 30-240 feet, about 25-275 feet, about 25-250 feet, about 30-180 feet, about 30-150 feet, about 25-100 feet, or about 30-90 feet), wherein the amount of release-resistant water in the material is indicative of the location of petroleum deposits in different areas of the petroleum well (aspect 91).

In aspects, the invention provides the method of any one of aspects 64-91, wherein the method is performed on one or more petroleum cuttings obtained from a low visibility play, such as on samples obtained from a fresh-water site (aspect 92).

In aspects, the invention provides the method of any one of aspects 79-92, wherein the steps of the method are performed within less than about 5 minutes (aspect 93).

In aspects, the invention provides the method of any one of aspects 64-93, wherein the method is performed on at least two petroleum drill cuttings obtained from a horizontal petroleum well (aspect 94).

In aspects, the invention provides the method of aspect 94, wherein more, such as at least about 75%, such as at least about 85% of the area of the horizontal petroleum well from which the samples are obtained is contained with a vertical zone of about 50 feet or less, such as about 20 feet or less, about 15 feet or less, or about 10 feet or less (aspect 95).

In aspects, the invention provides the method of any one of aspects 64-95, wherein the method is performed on one or more petroleum drill cuttings, the method is performed within five minutes, and the method is performed on cuttings that are less than about 20 minutes old, such as less than about 15 minutes old, such as less than about 12 minutes old, such as less than about 10 minutes old, such less than about 7 minutes old, such as less than about 5 minutes old, such as less than about 3 minutes old, such as less than about 2 minutes old, such as less than about 1 minute old (with respect to when such cutting reached the surface), such that the results of the analysis can inform the real time or near real time direction (steering) of the drilling operation (aspect 96).

In aspects, the invention provides a method for analyzing a material containing release-resistant water comprising: (a) removing at least about 99% of any water associated with the material that is removable from the material by subjecting the material to a temperature of at least about 100 degrees C. water at normal atmospheric pressure ("extraneous water") from the material to obtain extraneous water-free material; (b) measuring an amount of remaining water remaining in the material ("release-resistant water") without extracting the release-resistant water, and (c) using the measurement of the amount of release-resistant water to assess the characteristics of the material (aspect 97).

In aspects, the invention provides the method of aspect 97, wherein step (b) of the method comprises measuring water in the material in-situ through one or more of thermal gravimetric analyses, differential scanning calorimetry, spectroscopic methods such as NMR, MM, Raman spectroscopy, and Infrared Spectroscopy, and methods comprising weighing the material prior to and after removal of the extraneous water (aspect 98).

In aspects, the invention provides the method of aspect 97 or 98, wherein the method is repeatedly performed on material from different parts of a geologic unit, wherein the relative amounts of release-resistant water measured in each cycle from each sample is used to generate a map of one or more properties of the geologic unit derived from the measurements of release-resistant water (aspect 99).

In aspects, the invention provides the method of aspect 97, wherein the geologic unit is a geological site, e.g., a petroleum well (aspect 100).

In aspects, the invention provides a system for analyzing release-resistant water in materials comprising: (a) a collection component capable of capturing samples and delivering samples into an enclosed analytical device; (b) an optional washing component configured to wash delivered samples in an average time of about 1 minute or less; (c) a drying component capable of removing extraneous water from washed samples in an average time of about 2 minutes or less; and (d) an enclosed device comprising, (i) an optional sorting component for sorting samples from one another, (ii) an optional crushing component configured to crush the samples in an average time of about 1 minute or less, and (iii) an analytical component capable of analyzing the amount of release-resistant water in the dried material (aspect 101).

In aspects, the invention provides the system of aspect 101, wherein the analytical component comprises an in-situ water content analysis device or component that is capable of measuring release-resistant water still contained within samples after the removal of extraneous water (aspect 102).

In aspects, the invention provides the system of aspect 102, wherein the in-situ water content analysis device or component operates by a method that comprises one or more of capacitance manometry, thermal gravimetric analyses, differential scanning calorimetry, spectroscopic methods such as NMR, MM, Raman spectroscopy, and infrared spectroscopy, and weighing the material prior to and after removal of the extraneous water (aspect 103).

In aspects, the invention provides the system of aspect 103, wherein the enclosed device further comprises (iv) an extraction component capable of exerting an extraction force on the samples capable of extracting an analyzable amount of release-resistant water and wherein the analytical component analyzes release-resistant water extracted from samples (aspect 104).

In aspects, the invention provides the system of aspect 104, wherein the extraction component can extract an analyzable amount of release-resistant water from samples that the system is configured to analyze in an average time of about 2 minutes or less (aspect 105).

In aspects, the invention provides the system of any one of aspects 101-105, wherein the enclosed device comprises a first chamber containing the crushing component and a separate second chamber comprising the extraction component and that comprises or is in communication with the analytical component, wherein samples are capable of flowing from the first chamber to the second chamber under automated or selectively controlled conditions (aspect 106).

In aspects, the invention provides the system of any one of aspects 101-106, wherein the collection component comprises channels for permitting the passage of a flow of liquid containing solid samples (aspect 107).

In aspects, the invention provides the system of any one of aspects 101-107, wherein the enclosed device comprises one or more gating components, one or more tortuous path components, or both, to control the flow of samples through the enclosed device (aspect 108).

In aspects, the invention provides the system of any one of aspects 101-108, wherein the system further comprises a communication component for relaying data obtained from the analytical component to a well site operator (aspect 109).

In aspects, the invention provides the system of aspect 109, wherein the system includes a component for associating release-resistant water data associated with samples analyzed by the device with other analytical data for samples obtained from a comparable location of a geologic unit under study (aspect 110).

In aspects, the invention provides the system of aspect 110, wherein the other analytical data comprises wire log data, fluid inclusion analysis data, or non-fluid inclusion organic compound volatiles data (aspect 111).

In aspects, the invention provides a method for assessing the characteristics of a material comprising (a) placing a material in an enclosure such that the material is isolated from the environment; (b) removing substantially all of the extraneous water associated with the material, (c) removing substantially all of the released extraneous water from the enclosure; (d) applying an extracting force to the sample of material in the enclosure, wherein the extracting force is capable of causing the release of a detectable amount of water molecules, H2 gas, element(s), or ions which, individually or in combination(s), are indicative of the amount of water in the material, if present, and (e) measuring the amount of water molecules H2 gas, element(s), or ions released in the performance of step (d) using mass spectrometry (aspect 112).

In aspects, the invention provides the method of aspect 112, wherein the extracting force optionally means the combination of two or more forces; the extracting force is about equal in effectiveness in terms of removing release-resistant water to application of a vacuum at a pressure of about 2 millibars for a period of less than about 9 minutes; and wherein the conditions of the method are such that no more than 1% of the crystalline minerals present in the composition decompose and release their structural water in the performance of the method (aspect 113).

The invention claimed is:
1. A method for analyzing a material containing release-resistant water comprising:
 (a) applying a force to remove at least about 99% of any extraneous water present in the material, wherein the applied force is at least as effective as removing the extraneous water from the material by subjecting the material to at least 100 degrees Celsius at normal atmospheric pressure for a sufficient period of time to convert any such extraneous water to water vapor, to establish the material as at least essentially free of extraneous water but still containing at least a detectable amount of release-resistant water, wherein release-resistant water is water that is not removable by the applied force;
 (b) applying an additional extraction force to the material in the state resulting from step (a) of the method to extract a detectable amount of the release-resistant water contained in the material without causing the release of more than 1% of any water contained in crystalline mineral compounds in the material;
 (c) using capacitance manometry to measure the amount of release-resistant water obtained in step (b) of the method; and
 (d) using the measured amount of release-resistant water identified in step (c) of the method to assess one or more characteristics of the material.

2. The method of claim 1, wherein in step (b) of the method, the material is housed in a water impermeable, crushable container, and the additional extraction force applied to the material in step (b) of the method is a vacuum pressure that is at least as effective in extracting an amount of release-resistant water as applying a vacuum of about 2 millibars to a sample of 300-400 microliters of rock for a period of at least about 5 minutes in a water-impermeable, crushable cylindrical container having a diameter of about 0.25 inches and a length of about 3.5 inches.

3. The method of claim 2, wherein, prior to extracting the release-resistant water in step (b) of the method, the material is indirectly mechanically disrupted by applying a force to the water impermeable, crushable container housing the material during step (b) of the method without the escape of volatile compounds, release-resistant water, or both from the container.

4. The method of claim 3, wherein the release-resistant water contains no more than about 0.5% of the water contained in the crystalline mineral compounds in the material.

5. The method of claim 2, wherein during the removal of the extraneous water from the material in step (a) of the method, a vacuum pressure is further applied to the material which extracts a measurable amount of organic volatile compounds from the material, wherein at least about 70% of the extracted organic volatile compounds were not contained in fluid inclusions in the material prior to extraction from the material in step (a) of the method.

6. The method of claim 1, wherein the method is repeated at least 10 times, each repetition of the method performed on a material obtained from a different location in a petroleum well, wherein the relationship between the amount of the release-resistant water released from each of the materials is indicative of the location of one or more petroleum deposits in one or more different locations of the petroleum well.

7. The method of claim 6, wherein the petroleum well is a horizontal petroleum well, and at least about 85% of the horizontal petroleum well is contained within a vertical zone of about 20 feet or less.

8. The method of claim 1, wherein an upper limit to the additional extraction force or force applied in step (b) of the method is established to ensure that the material is not damaged such that a sufficient amount of the water contained in the crystalline mineral compounds in the material to interfere with the correct measurement of release-resistant water is not released.

9. The method of claim 1, wherein the release-resistant water contains no more than about 0.5% of the water contained in the crystalline mineral compounds in the material.

10. The method of claim 1, wherein the release-resistant water contains no more than about 0.1% of the water contained in the crystalline mineral compounds in the material.

11. A method for analyzing a material containing release-resistant water comprising:
 (a) applying a force to remove at least about 99% of any extraneous water present in the material, wherein the applied force is at least as effective as removing the extraneous water from the material by subjecting the material to at least 100 degrees Celsius at normal atmospheric pressure for a sufficient period of time to convert any such extraneous water to water vapor, to establish the material as at least essentially free of extraneous water but still containing at least a detectable amount of release-resistant water, wherein release-resistant water is water that is not removable by the applied force;
 (b) applying an additional extraction force to the material in the state resulting from step (a) of the method to extract a detectable amount of the release-resistant water contained in the material without causing the release of more than 1% of any water contained in crystalline mineral compounds in the material;
 (c) measuring the amount of release-resistant water obtained in step (b) of the method; and
 (d) using the measured amount of the release-resistant water identified in step (c) of the method to assess one or more characteristics of the material.

12. The method of claim 11, wherein the measurement of the release-resistant water in step (c) of the method comprises analysis by capacitance manometry, humidity metrics, chemical assay, or calculation of a change in mass of the material.

13. The method of claim 12, wherein the measurement of the release-resistant water in step (c) of the method is performed using capacitance manometry.

14. The method of claim 11, wherein the method is repeated two or more times using two or more different material samples.

15. The method of claim 14, wherein the two or more different material samples are two or more material samples from a geologic unit.

16. The method of claim 15, wherein the two or more material samples from the geologic unit are each petroleum drill cuttings collected from a single geologic site or from two or more related geological sites within the geological unit.

17. The method of claim 16, wherein removing the extraneous water from the material in step (a) of the method comprises physically drying the petroleum drill cuttings, applying heat to the petroleum drill cuttings, applying a vacuum to the petroleum drill cuttings, chemically drying the petroleum drill cuttings, or performing a combination of any two or more thereof to the petroleum drill cuttings.

18. The method of claim 17, wherein the entire step of removing the extraneous water in step (a) of the method is performed at a temperature of less than about 100 degrees Celsius.

19. The method of claim 18, wherein removing the extraneous water from the material in step (a) of the method comprises applying a vacuum force that has at least a significantly similar water removal efficacy as applying a vacuum of about 20 millibars to a sample of 300-400 microliters of rock, housed in a cylindrical container that is impermeable with respect to water and which has a diameter of about 0.25 inches and a length of about 3.5 inches, for a period of at least about 5 minutes.

20. The method of claim 14, wherein one or more of steps (a)-(d) of the method are automatically performed in response to a computer-implemented controller that comprises one or more preprogrammed conditions, one or more computer-generated conditions, or both one or more preprogrammed conditions and one or more computer-generated conditions, related to the timing of the performance of such one or more of steps (a)-(d), related to the conditions under which such one or more of steps (a)-(d) are performed, or related to both the timing and conditions of such one or more of steps (a)-(d).

21. The method of claim 11, wherein removing the extraneous water from the material in step (a) of the method comprises subjecting the material to a vacuum pressure that extracts a measurable amount of organic volatile compounds from the material, wherein at least about 70% of the organic volatile materials were not contained in fluid inclusions present within the material prior to their extraction from the material in step (a) of the method.

22. The method of claim 11, wherein the release-resistant water contains no more than about 0.5% of the water contained in the crystalline mineral compounds in the material.

23. The method of claim 11, wherein the release-resistant water contains no more than about 0.1% of the water contained in the crystalline mineral compounds in the material.

* * * * *